United States Patent
Canady et al.

(10) Patent No.: US 12,137,958 B2
(45) Date of Patent: *Nov. 12, 2024

(54) SYSTEM AND METHOD FOR ELECTROSURGICAL CONDUCTIVE GAS CUTTING FOR IMPROVING ESCHAR, SEALING VESSELS AND TISSUES

(71) Applicant: U.S. Patent Innovations, LLC, Takoma Park, MD (US)

(72) Inventors: Jerome Canady, Lakeland, FL (US); Edson Vieira, Ribeirao Preto (BR); Nicholas Vieira, Ribeirao Preto (BR); Kimberly Wiley, Rochester, NY (US)

(73) Assignee: U.S. Patent Innovations, LLC, Takoma Park, MD (US)

( * ) Notice: Subject to any disclaimer, the term of this patent is extended or adjusted under 35 U.S.C. 154(b) by 219 days.

This patent is subject to a terminal disclaimer.

(21) Appl. No.: 17/014,255

(22) Filed: Sep. 8, 2020

(65) Prior Publication Data

US 2021/0007787 A1 Jan. 14, 2021

Related U.S. Application Data

(63) Continuation of application No. 16/050,482, filed on Jul. 31, 2018, now Pat. No. 10,765,468, which is a
(Continued)

(51) Int. Cl.
*A61B 18/04* (2006.01)
*A61B 18/00* (2006.01)
*A61N 1/44* (2006.01)

(52) U.S. Cl.
CPC .. *A61B 18/042* (2013.01); *A61B 2018/00607* (2013.01); *A61N 1/44* (2013.01)

(58) Field of Classification Search
CPC ... A61B 18/042; A61B 18/14; A61B 18/1482; A61B 2018/00589; A61B 2018/00601;
(Continued)

(56) References Cited

U.S. PATENT DOCUMENTS 3,239,730 A 3/1966 Farago
3,699,967 A 10/1972 Anderson
(Continued)

FOREIGN PATENT DOCUMENTS

WO 03028542 4/2003

OTHER PUBLICATIONS

A. Erwine, "ESU-2000 Series Product Overview A Paradigm Shift in Electrosurdery Testing Technology and Capability Is Here," BC Group International, Inc. (2007).
(Continued)

*Primary Examiner* — Michael F Peffley
(74) *Attorney, Agent, or Firm* — 24IP Law Group USA, PLLC; Timothy R DeWitt

(57) ABSTRACT

An electrosurgical method and device for simultaneously cutting and coagulating tissue with an electrosurgical device having an electrode and a channel wherein said channel has a port near a proximal end of said electrode, wherein the method comprises the steps of causing an inert gas to flow through said channel and exit said port, applying high-frequency energy to said electrode while said inert gas flows through said channel, wherein said high-frequency energy applied to said electrode continuously plasmatizes inert gas exiting said port, initiating an electrical discharge from said electrode through said continuously plasmatized inert gas to said tissue, cutting tissue with said electrode, maintaining said electrical discharge from said electrode through said
(Continued)

plasmatized inert gas while cutting tissue with said electrode to cause coagulation of said tissue simultaneously with said cutting.

4 Claims, 52 Drawing Sheets

Related U.S. Application Data continuation of application No. 13/882,010, filed as application No. PCT/US2011/059025 on Nov. 2, 2011, now Pat. No. 10,052,146.

(60) Provisional application No. 61/550,905, filed on Oct. 24, 2011, provisional application No. 61/409,138, filed on Nov. 2, 2010.

(58) Field of Classification Search
CPC .. A61B 2018/1213; A61B 2018/00577; A61B 2018/1412; A61B 2018/1475; A61B 2018/00607; A61B 2018/122; A61B 2018/1425; A61B 2018/00595
See application file for complete search history.

(56) References Cited

U.S. PATENT DOCUMENTS

| | | | |
|---|---|---|---|
| 4,040,426 A | 8/1977 | Morrison | |
| 4,429,694 A | 2/1984 | Mcgreevy | |
| 4,580,562 A | 4/1986 | Goof et al. | |
| 4,781,175 A | 11/1988 | McGreevy | |
| 5,088,997 A | 2/1992 | Delahuerga et al. | |
| 5,098,430 A * | 3/1992 | Fleenor | A61B 18/1402 606/49 |
| 5,207,675 A | 5/1993 | Canady | |
| 5,217,457 A | 6/1993 | Delahuerga | |
| 5,256,138 A * | 10/1993 | Burek | A61B 18/042 606/49 |
| 5,306,238 A * | 4/1994 | Fleenor | A61B 18/042 606/49 |
| 5,370,675 A * | 12/1994 | Edwards | A61B 18/1477 607/116 |
| 5,449,356 A | 9/1995 | Walbrink et al. | |
| 5,693,044 A * | 12/1997 | Cosmescu | A61B 18/042 606/49 |
| 5,800,427 A | 9/1998 | Zamba | |
| 6,149,648 A | 11/2000 | Cosmescu | |
| 6,325,799 B1 | 12/2001 | Goble | |
| 6,409,724 B1 | 6/2002 | Penney et al. | |
| 6,458,125 B1 * | 10/2002 | Cosmescu | A61B 18/042 606/41 |
| 6,494,881 B1 | 12/2002 | Bales et al. | |
| 7,517,347 B2 | 4/2009 | Hug et al. | |
| 2003/0097129 A1 | 5/2003 | Davison et al. | |
| 2006/0052774 A1 | 3/2006 | Garrison et al. | |
| 2006/0122595 A1 * | 6/2006 | Farin | A61B 18/042 606/49 |
| 2007/0029500 A1 | 2/2007 | Coulombe | |
| 2007/0213704 A1 | 9/2007 | Truckai et al. | |
| 2007/0225699 A1 | 9/2007 | Goble | |
| 2009/0248022 A1 | 10/2009 | Falkenstein et al. | |
| 2011/0112528 A1 | 5/2011 | Steiber et al. | |

OTHER PUBLICATIONS

"Force Argon II System," Valleylab 2006.
"Argon-Plasma Koagulation," GMS Krankenhaushygiene Interdisziplinar 2008, vol. 3(1), ISSN 1863-5245.
"Valleylab Force Argon II Argon Enhanced Electrosurgical System," 1997.

* cited by examiner

| Power (W) | ΔT, °C |
|---|---|
| 20 | 38.9 |
| 40 | 53.5 |
| 60 | 46.2 |
| 80 | 51.0 |
| 100 | 53.5 |

| Power (W) | Length, mm |
|---|---|
| 20 | 0.8 |
| 40 | 2.0 |
| 60 | 2.5 |
| 80 | 2.5 |
| 100 | 3.0 |

ΔT, °C

| Power (W)/Flow(l/min) | 0.5 | 1.5 | 2.5 | 5 |
|---|---|---|---|---|
| 20 | 43.7 | 53.5 | 48.6 | 38.9 |
| 40 | 53.5 | 38.9 | 43.7 | 68.0 |
| 60 | 48.6 | 34.0 | 38.9 | 63.2 |
| 80 | 43.7 | 34.0 | 38.9 | 48.6 |
| 100 | 43.7 | 38.9 | 58.3 | 48.6 |

FIG. 5E

Length, mm

| Power (W)/Flow(l/min) | 0.5 | 1.5 | 2.5 | 5 |
|---|---|---|---|---|
| 20 | 0.9 | 4.3 | 3.6 | 5.4 |
| 40 | 3.8 | 7.3 | 8.1 | 8.5 |
| 60 | 3.8 | 11.3 | 10.4 | 9.4 |
| 80 | 3.8 | 15.2 | 11.3 | 11.9 |
| 100 | 4.4 | 15.3 | 11.8 | 13.0 |

FIG. 5F

| Power (W) | ΔT, °C |
|---|---|
| 20 | 32.8 |
| 40 | 62.0 |
| 60 | 61.6 |
| 80 | 82.6 |
| 100 | 71.3 |
| 120 | 81.0 |
| 200 | 77.8 |

| Power (W)/Flow(l/min) | ΔT, °C | | | |
|---|---|---|---|---|
| | 0.5 | 1.5 | 2.5 | 5 |
| 20 | 29.2 | 34.0 | 36.5 | 38.9 |
| 40 | 43.7 | 48.6 | 48.6 | 43.7 |
| 60 | 48.6 | 72.9 | 72.9 | 58.3 |
| 80 | 63.2 | 87.5 | 77.8 | 48.6 |
| 100 | 58.3 | 87.5 | 72.9 | 53.5 |
| 120 | 63.2 | 82.6 | 77.8 | 68.0 |

| Power (W) | ΔT, °C |
|---|---|
| 20 | 19.4 |
| 40 | 34.0 |
| 60 | 35.0 |
| 80 | 38.9 |
| 100 | 43.7 |
| 120 | 43.7 |

FIG. 8B

| Power (W) | Length, mm |
|---|---|
| 20 | 1.5 |
| 40 | 2.0 |
| 60 | 2.0 |
| 80 | 2.5 |
| 100 | 3.4 |
| 120 | 3.4 |

| Power (W)/ Flow(l/min) | 0.1 | 1 | 3 | 7 | 10 |
|---|---|---|---|---|---|
| 20 | 29.2 | 24.3 | 24.3 | 19.4 | 14.6 |
| 40 | 43.7 | 24.3 | 29.2 | 19.4 | 19.4 |
| 60 | 48.6 | 29.2 | 34.0 | 29.2 | 29.2 |
| 80 | 48.6 | 34.0 | 38.9 | 38.9 | 38.9 |
| 100 | 43.7 | 43.7 | 48.6 | 43.7 | 43.7 |
| 120 | 48.6 | 68.0 | 63.2 | 43.7 | 68.0 |

FIG. 9E

Length, mm

| Power (W)/ Flow(l/min) | 0.1 | 1 | 3 | 7 | 10 |
|---|---|---|---|---|---|
| 20 | 1.5 | 6.0 | 8.5 | 9.0 | 5.3 |
| 40 | 2.0 | 11.8 | 12.0 | 11.2 | 10.0 |
| 60 | 3.0 | 15.4 | 15.1 | 10.0 | 10.1 |
| 80 | 3.1 | 15.5 | 15.1 | 14.7 | 12.8 |
| 100 | 2.7 | 18.0 | 16.0 | 16.0 | 15.8 |
| 120 | 3.2 | 19.0 | 15.9 | 15.9 | 16.4 |

FIG. 9F

| Power (W) | ΔT, °C |
|---|---|
| 20 | 29.2 |
| 40 | 29.2 |
| 60 | 38.9 |
| 80 | 38.9 |
| 100 | 38.9 |
| 120 | 43.7 |
| 200 | 82.6 |

ΔT, °C

| Power (W)/ Flow(l/min) | 0.1 | 1 | 3 | 7 | 10 |
|---|---|---|---|---|---|
| 20 | 14.6 | 19.4 | 24.3 | 24.3 | 24.3 |
| 40 | 24.3 | 24.3 | 38.9 | 29.2 | 24.3 |
| 60 | 29.2 | 34.0 | 34.0 | 29.2 | 29.2 |
| 80 | 38.9 | 38.9 | 34.0 | 29.2 | 38.9 |
| 100 | 43.7 | 38.9 | 34.0 | 34.0 | 38.9 |
| 120 | 34.0 | 48.6 | 38.9 | 29.2 | 63.2 |

FIG. 11C

A - Conventional Cut

|     | Power (W) | Flow (L/min) | Diameter (mm) |
|-----|-----------|--------------|---------------|
| A-1 | 20        | ---          | 3.09          |
| A-2 | 40        | ---          | 2.83          |
| A-3 | 60        | ---          | 2.83          |
| A-4 | 80        | ---          | 4.23          |
| A-5 | 100       | ---          | 4.81          |
| A-6 | 120       | ---          | 5.04          |
| A-7 | 150       | ---          | 5.14          |

B - Conventional Coag

|  | Power (W) | Flow (L/min) | Diameter (mm) |
|---|---|---|---|
| B-1 | 20 | --- | 5.13 |
| B-2 | 40 | --- | 6.74 |
| B-3 | 60 | --- | 8.45 |
| B-4 | 80 | --- | 10.64 |
| B-5 | 100 | --- | 9.66 |

C - Argon Coagulation

|  | Power (W) | Flow (L/min) | Diameter (mm) |
|---|---|---|---|
| C-1 | 20 | 0.5 | 7.76 |
| C-2 | 20 | 1.5 | 8.77 |
| C-3 | 20 | 2.5 | 8.78 |
| C-4 | 20 | 5.0 | 8.78 |
| C-5 | 40 | 0.5 | 8.81 |
| C-6 | 40 | 1.5 | 8.51 |
| C-7 | 40 | 2.5 | 8.88 |
| C-8 | 40 | 5.0 | 9.65 |
| C-9 | 60 | 0.5 | 9.93 |
| C-10 | 60 | 1.5 | 9.56 |
| C-11 | 60 | 2.5 | 9.65 |
| C-12 | 60 | 5.0 | 10.36 |
| C-13 | 80 | 0.5 | 10.31 |
| C-14 | 80 | 1.5 | 10.31 |
| C-15 | 80 | 2.5 | 11.35 |
| C-16 | 80 | 5.0 | 12.13 |
| C-17 | 100 | 0.5 | 13.28 |
| C-18 | 100 | 1.5 | 12.36 |
| C-19 | 100 | 2.5 | 12.38 |
| C-20 | 100 | 5.0 | 12.24 |

FIG. 15A

Table 16.
D – Hybrid Plasma Cut SS-200E/Argon 2

|  | Power (W) | Flow (L/min) | Diameter (mm) |
| --- | --- | --- | --- |
| D-2 | 20 | 0.5 | 2.60 |
| D-3 | 20 | 2.5 | 2.33 |
| D-4 | 20 | 5.0 | 2.20 |
| D-7 | 40 | 0.5 | 2.46 |
| D-8 | 40 | 2.5 | 2.47 |
| D-9 | 40 | 5.0 | 4.42 |
| D-12 | 60 | 0.5 | 4.38 |
| D-13 | 60 | 2.5 | 5.07 |
| D-14 | 60 | 5.0 | 3.90 |
| D-17 | 80 | 0.5 | 3.94 |
| D-18 | 80 | 2.5 | 3.94 |
| D-19 | 80 | 5.0 | 6.10 |
| D-22 | 100 | 0.5 | 3.38 |
| D-23 | 100 | 2.5 | 3.86 |
| D-24 | 100 | 5.0 | 4.31 |
| D-27 | 120 | 0.5 | 2.52 |
| D-28 | 120 | 2.5 | 3.72 |
| D-29 | 120 | 5.0 | 5.73 |
| D-32 | 150 | 0.5 | 8.44 |
| D-33 | 150 | 2.5 | 7.86 |
| D-34 | 150 | 5.0 | 6.88 |

FIG. 16A

E – Hybrid Cut SS-601MCa/Argon 4

|  | Power (W) | Flow (L/min) | Diameter (mm) |
|---|---|---|---|
| E-1 | 20 | 0.1 | 2.50 |
| E-2 | 20 | 1.0 | 2.51 |
| E-3 | 20 | 3.0 | 1.21 |
| E-4 | 20 | 7.0 | 1.75 |
| E-5 | 20 | 10.0 | 1.38 |
| E-6 | 40 | 0.1 | 1.78 |
| E-7 | 40 | 1.0 | 2.05 |
| E-8 | 40 | 3.0 | 2.00 |
| E-9 | 40 | 7.0 | 1.90 |
| E-10 | 40 | 10.0 | 1.59 |
| E-11 | 60 | 0.1 | 1.59 |
| E-12 | 60 | 1.0 | 1.81 |
| E-13 | 60 | 3.0 | 2.02 |
| E-14 | 60 | 7.0 | 2.46 |
| E-15 | 60 | 10.0 | 1.66 |
| E-16 | 80 | 0.1 | 2.51 |
| E-17 | 80 | 1.0 | 2.04 |
| E-18 | 80 | 3.0 | 2.55 |
| E-19 | 80 | 7.0 | 1.69 |
| E-20 | 80 | 10.0 | 2.63 |
| E-21 | 100 | 0.1 | 2.56 |
| E-22 | 100 | 1.0 | 2.21 |
| E-23 | 100 | 3.0 | 1.77 |
| E-24 | 100 | 7.0 | 2.04 |
| E-25 | 100 | 10.0 | 5.80 |
| E-26 | 120 | 0.1 | 2.47 |
| E-27 | 120 | 1.0 | 2.94 |
| E-28 | 120 | 3.0 | 2.49 |
| E-29 | 120 | 7.0 | 7.53 |
| E-30 | 120 | 10.0 | 7.81 |
| E-31 | 150 | 0.1 | 5.82 |
| E-32 | 150 | 1.0 | 8.75 |
| E-33 | 150 | 3.0 | 9.78 |
| E-34 | 150 | 7.0 | 9.58 |
| E-35 | 150 | 10.0 | 9.59 |

FIG. 17A

Conventional Cut

|    | Power (W) | Depth Injury (mm) |
|----|-----------|-------------------|
| A1 | 20        | 1.2               |
| A2 | 40        | 0.4               |
| A3 | 60        | 1.6               |
| A4 | 80        | 3.7               |
| A5 | 100       | 2.5               |
| A6 | 120       | 3.3               |
| A7 | 150       | 3.5               |

FIG. 18A

Conventional Coag

|    | Power (W) | Depth Injury (mm) |
|----|-----------|-------------------|
| B1 | 20        | 1.5               |
| B2 | 40        | 2.5               |
| B3 | 60        | 3.6               |
| B4 | 80        | 3.6               |
| B5 | 100       | 4.0               |

FIG. 18B

Argon Coag

|     | Power (W) | Flow (L/min) | Depth Injury (mm) |
|-----|-----------|--------------|-------------------|
| C1  | 20        | 0.5          | 0.6               |
| C2  | 20        | 1.5          | 0.7               |
| C3  | 20        | 2.5          | 0.5               |
| C4  | 20        | 5.0          | 0.5               |
| C5  | 40        | 0.5          | 0.8               |
| C6  | 40        | 1.5          | 0.9               |
| C7  | 40        | 2.5          | 1.0               |
| C8  | 40        | 5.0          | 1.2               |
| C9  | 60        | 0.5          | 1.3               |
| C10 | 60        | 1.5          | 1.1               |
| C11 | 60        | 2.5          | 1.1               |
| C12 | 60        | 5.0          | 1.1               |
| C13 | 80        | 0.5          | 1.6               |
| C14 | 80        | 1.5          | 1.3               |
| C15 | 80        | 2.5          | 1.3               |
| C16 | 80        | 5.0          | 1.5               |
| C17 | 100       | 0.5          | 0.7               |
| C18 | 100       | 1.5          | 1.1               |
| C19 | 100       | 2.5          | 1.1               |
| C20 | 100       | 5.0          | 1.1               |

FIG. 18C

Hybrid Plasma Cut @ SS-200E and Argon2

|  | Power (W) | Flow (L/min) | Depth Injury (mm) |
|---|---|---|---|
| D2 | 20 | 0.5 | 0.4 |
| D3 | 20 | 2.5 | 0.4 |
| D4 | 20 | 5.0 | 0.4 |
| D7 | 40 | 0.5 | 1.2 |
| D8 | 40 | 2.5 | 1.4 |
| D9 | 40 | 5.0 | 0.3 |
| D12 | 60 | 0.5 | 2.1 |
| D13 | 60 | 2.5 | 1.5 |
| D14 | 60 | 5.0 | 1.5 |
| D17 | 80 | 0.5 | 2.5 |
| D18 | 80 | 2.5 | 0.7 |
| D19 | 80 | 5.0 | 1.2 |
| D22 | 100 | 0.5 | 1.4 |
| D23 | 100 | 2.5 | 1.2 |
| D24 | 100 | 5.0 | 1.1 |
| D27 | 120 | 0.5 | 1.6 |
| D28 | 120 | 2.5 | 1.7 |
| D29 | 120 | 5.0 | 1.2 |
| D32 | 150 | 0.5 | 2.7 |
| D33 | 150 | 2.5 | 2.5 |
| D34 | 150 | 5.0 | 1.9 |

FIG. 18D

Hybrid Plasma Cut @ SS-601MCa and Argon4

|  | Power (W) | Flow (L/min) | Depth Injury (mm) |
|---|---|---|---|
| E1 | 20 | 0.1 | 0.1 |
| E2 | 20 | 1.0 | 0.1 |
| E3 | 20 | 3.0 | 0.1 |
| E4 | 20 | 7.0 | 1.2 |
| E5 | 20 | 10.0 | 0.4 |
| E6 | 40 | 0.1 | 0.2 |
| E7 | 40 | 1.0 | 1.0 |
| E8 | 40 | 3.0 | 3.0 |
| E9 | 40 | 7.0 | 1.0 |
| E10 | 40 | 10.0 | 0.1 |
| E11 | 60 | 0.1 | 0.1 |
| E12 | 60 | 1.0 | 0.5 |
| E13 | 60 | 3.0 | 3.7 |
| E14 | 60 | 7.0 | 0.1 |
| E15 | 60 | 10.0 | 0.15 |
| E16 | 80 | 0.1 | 1.1 |
| E17 | 80 | 1.0 | 0.7 |
| E18 | 80 | 3.0 | 1.7 |
| E19 | 80 | 7.0 | 0.7 |
| E20 | 80 | 10.0 | 3.1 |
| E21 | 100 | 0.1 | 1.9 |
| E22 | 100 | 1.0 | 2.1 |
| E23 | 100 | 3.0 | 2.0 |
| E24 | 100 | 7.0 | 1.8 |
| E25 | 100 | 10.0 | 5.4 |
| E26 | 120 | 0.1 | 1.4 |
| E27 | 120 | 1.0 | 2.0 |
| E28 | 120 | 3.0 | 3.1 |
| E29 | 120 | 7.0 | 6.6 |
| E30 | 120 | 10.0 | 7.2 |
| E31 | 150 | 0.1 | 5.3 |
| E32 | 150 | 1.0 | 5.0 |
| E33 | 150 | 3.0 | 4.8 |
| E34 | 150 | 7.0 | 4.4 |
| E35 | 150 | 10.0 | 4.9 |

FIG. 18E

Argon Coag: Depth of injury not very dependant on flow rate

SYSTEM AND METHOD FOR ELECTROSURGICAL CONDUCTIVE GAS CUTTING FOR IMPROVING ESCHAR, SEALING VESSELS AND TISSUES

CROSS-REFERENCE TO RELATED APPLICATIONS

The present application is a continuation of U.S. patent application Ser. No. 16/050,482 filed Jul. 31, 2018, now U.S. Pat. No. 10,765,468, which is a continuation of U.S. patent application Ser. No. 13/882,010 filed Jul. 18, 2013, now U.S. Pat. No. 10,052,146, which is a U.S. National Stage of PCT Application No. PCT/US2011/059025 filed on Nov. 2, 2011, which claims the benefit of the filing date of U.S. Provisional Patent Application Ser. No. 61/409,138 filed by the present inventors on Nov. 2, 2010 and U.S. Provisional Patent Application Ser. No. 61/550,905 filed by the present inventors on Oct. 24, 2011.

The aforementioned patent applications are hereby incorporated by reference in their entirety.

STATEMENT REGARDING FEDERALLY SPONSORED RESEARCH OR DEVELOPMENT

None.

BACKGROUND OF THE INVENTION

Field of the Invention

The present invention relates to electrosurgical systems and methods, and more particularly, electrosurgical systems and methods using plasma during cutting modes of operation.

Brief Description of the Related Art

The standard means for controlling traumatic and surgical blood loss are electrosurgical generators and lasers which respectively direct high-frequency electrical currents or light energy to localize heat in bleeding vessels to coagulate the overlying blood and vessel walls. Hemostasis and tissue destruction are of critical importance when removing abnormal tissue during surgery and therapeutic endoscopy. For monopolar electrosurgery electrical energy originates from an electrosurgical generator and is applied to target tissue via an active electrode that typically has a small cross-sectional surface-area to concentrate electrical energy at the surgical site. An inactive return electrode or patient plate that is large relative to the active electrode contacts the patient at a location remote from the surgical site to complete and electrical circuit through the tissue. For bipolar electrosurgery, a pair of active electrodes are used and electrical energy flows directly through the tissue between the two active electrodes.

U.S. Pat. No. 4,429,694 to McGreevy disclosed a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect and a desiccation effect. Fulguration and desiccation sometimes are referred to collectively as coagulation.

A conventional desiccation procedure, shown in FIG. 1B, typically is performed by holding the active electrode in contact with the tissue. Radiofrequency (RF) current passes from the electrode directly into the tissue to produce heating of the tissue by electrical resistance heating. The heating effect destroys the tissue cells and produces an area of necrosis spreading radially from the point of contact between the electrode and the tissue. The necrosis is usually deep.

A conventional fulguration procedure, shown in FIG. 1A, may be obtained by varying the voltage and power applied by the electrosurgical generator. Conventional fulguration procedures typically were performed using a waveform which has a high peak voltage but a low duty cycle. If the active electrode was brought close to but not touching the tissue and the peak voltage was sufficient to produce an RF arc, fulguration would occur at the point where the arc contacted the tissue. Due to the low duty cycle, the power per unit time applied to the tissue was low enough so that cutting effects were minimized.

A conventional cutting procedure, shown in FIG. 1C, may be obtained by delivering sufficient power per unit time to the tissue to vaporize cell moisture. If the power applied is high enough a sufficient amount of steam is generated to form a steam layer between the active electrode and the tissue. When the steam layer forms, a plasma consisting of highly ionized air and water molecules forms between the electrode and the tissue. An RF arc then develops in the plasma. At the location where the arc contacts the tissue, the power density becomes extremely high and instantaneously disrupts the tissue architecture. New steam is thereby produced to maintain the steam layer. If the power density is sufficient, enough cells are destroyed to cause a cutting action to occur. A repetitive voltage wave form, such as a sinusoid, delivers a continuous succession of arcs and produces a cut with very little necrosis and little hemostasis.

It also was possible to create a combined combination of effects by varying the electrical waveform applied to the tissue. Specifically, a combination of conventional cutting and desiccation could be produced by periodically interrupting the continuous sinusoidal voltage typically used to perform a conventional cutting procedure. If the interruption was sufficient, the ionized particles in the plasma between the electrode and the tissue would collapse, causing the electrode to momentarily come into contact with the tissue. That touching would desiccate the tissue thereby sealing off blood vessels in the vicinity of the electrode.

Conventional electrosurgical generators typically have both "cut" or cutting and "coag" or coagulation modes of operation. As previously noted, the cut mode typically will have a low voltage waveform form with a high duty cycle, e.g. 100%. The coag mode of an electrosurgical generator typically creates a waveform with large amplitude but short duration "spikes" to achieve hemostasis (coagulation). For example, in coag mode an electrosurgical generator may use a high voltage wave form at a 6% duty cycle. The surrounding tissue is heated when the waveform spikes and then cools down (between spikes), producing coagulation of the cells. Fulguration is achieved in the coag mode of the electrosurgical generator, with the tip of the surgical "active electrode" held above (but not in contact with) the tissue. Electrosurgical desiccation is achieved in either the cut or coag modes of the generator. The difference between desiccation and fulguration is the tip of the "active electrode" must contact the tissue as in FIG. 1B to achieve desiccation. Typically, the more desired mode to achieve tissue desiccation through direct tissue contact is the cut mode. Different degrees of hemostasis (coagulation) can be achieved by utilizing varying degrees of "Blended" waveforms, e.g., 50% on/50% off, 40% on/60% off, or 25% on/75% off.

Another method of monopolar electrosurgery using inert gas together with electrosurgical energy was described by Morrison U.S. Pat. No. 4,040,426 in 1977 and McGreevy U.S. Pat. No. 4,781,175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

APC has been demonstrated to be effective in the coagulation of blood vessels and human tissue during surgery. APC functions in a noncontact manner. The electrical current is initiated only when the tip of the handpiece or catheter is within one centimeter of the target tissue and produces a homogenous 1 mm to 2 mm well-delineated eschar. The eschar created by APC is further characterized by a decrease absence of charring and carbonization compare to eschar resulting from conventional electrosurgical fulguration. The eschar remains firmly attached to the tissue, in contrast to other coagulation modalities where there is an overlying charred layer of coagulated blood. There is minimal tissue necrosis with APC.

In U.S. Pat. Nos. 5,217,457 and 5,088,997 to Delahuerga et al. disclosed a device for performing procedure referred to as "argon shrouded cut." The device was an electrosurgical pencil having an exposed electrode with a distal end defining a tip for cutting biological tissue and a nose piece mounted about the electrode to define a pathway for a stream of inert gas which shrouds the electrode at or near its tip. When in coagulation mode, a convergent stream of inert gas was directed directly onto the tip of the electrode. In coagulation mode, the voltage was sufficient to initiate an electrical discharge in the inert gas. In cut mode, the stream of ionized gas was directed to impinge obliquely on the electrode at a point adjacent to but away from the tip of the electrode. In cutting mode, the open circuit voltage was generally not high enough to continuously plasmatize the inert gas and initiate and maintain an electrical discharge. Accordingly, in cut mode the function of the inert gas is to provide a shroud around the electrode rather than to initiate electrical discharge.

A multitude of literature exists that discloses and discusses various commercially available electrosurgical generators, voltage waveforms produced by those generators, and gas control units for use in various types of gas-assisted electrosurgery such as APC. For example, A. Erwine, "ESU-2000 Series Product Overview A Paradigm Shift in Electrosurgery Testing Technology and Capability Is Here," BC Group International, Inc. (2007) describes electrosurgical generators from ERBE Elektromedizin GmbH and ConMed Corporation, among others.

SUMMARY OF THE INVENTION

In a preferred embodiment, the present invention is an electrosurgical method for simultaneously cutting and coagulating tissue with an electrosurgical device having an electrode and a channel wherein said channel has a port near a proximal end of said electrode for directing a gas onto said proximal end of said electrode. The method comprises the steps of causing a gas to flow through said channel and exit said port, applying high-frequency energy to said electrode while said gas flows through said channel, wherein said high-frequency energy applied to said electrode continuously plasmatizes gas exiting said port, initiating an electrical discharge from said electrode through said continuously plasmatized gas to said tissue, cutting tissue with said electrode, maintaining said electrical discharge from said electrode through said plasmatized gas while cutting tissue with said electrode to cause coagulation of tissue adjacent said proximal end of said electrode simultaneously with said cutting. The gas may comprise an inert gas such as argon. The step of applying high-frequency energy to said electrode may comprise applying 70-100 W of power to said electrode. The step of causing a gas to flow through said channel may comprise causing an inert gas to flow through said channel at a flow rate of 7 L/min. The electrosurgical device is connected to an electrosurgical generator, said generator having a cut mode comprising a repeating voltage waveform and a coag mode comprising a varying voltage waveform, and wherein said step of applying high-frequency energy to said electrode comprises activating said electrosurgical generator in said cut mode. The repeating voltage waveform may be a sinusoidal waveform. The inert gas may exit the port in a direction substantially parallel to said electrode. A portion of said channel adjacent said port in said channel may be held at an angle of 45° to 60° to a surface of target tissue. The simultaneously cutting and coagulating causes a low depth of injury to the tissue and a small diameter of injury to said tissue.

In another embodiment, the present invention is an electrosurgical device. The device comprises means for initiating an electrical discharge from an electrode through continuously plasmatized inert gas to tissue and means for simultaneously cutting tissue with an energized electrode and coagulating said tissue by maintaining said electrical discharge from said electrode through said plasmatized inert gas while cutting said tissue with said energized electrode. The means for simultaneously cutting tissue and coagulating said tissue using a plasmatized inert gas may comprise a housing having an opening at a distal end, an electrode extending from said distal end of said housing, a channel within said housing, said channel having a port adjacent said electrode extending from said housing, means for causing an inert gas to flow through said channel and exit said port, means for applying high-frequency energy to said electrode while said inert gas flows through said channel, wherein said high-frequency energy applied to said electrode continuously plasmatizes inert gas exiting said port, means for initiating an electrical discharge from said electrode through said continuously plasmatized inert gas to said tissue, and means for maintaining said electrical discharge from said electrode through said plasmatized inert gas while cutting tissue with said electrode to cause coagulation of said tissue simultaneously with said cutting. The electrosurgical device may further comprise telescoping nozzle connected to said housing, wherein said telescoping nozzle is adjustable to change a length of said electrode extending from the housing. The electrode extends 2-25 mm from said telescoping nozzle.

In a preferred embodiment, the electrosurgical device comprises a housing, an electrode, wherein the electrode extends through the housing and a portion of the electrode extends from a distal end of the housing, a connector for connecting the electrode to an electrosurgical generator, a channel in the housing, a port at a proximate end of the channel for connecting the channel to a source of pressurized inert gas, and a port at a distal end of the channel for discharging inert gas flowing through the channel, and controls for initiating a flow of an inert gas through the channel and applying high-frequency electrical energy to the electrode, wherein the controls provide for a conventional cut mode, a conventional coagulation mode, an argon plasma coagulation mode, and a plasma cut mode. The plasma cut mode comprises maintaining an electrical discharge from the electrode through plasmatized inert gas being discharged from the channel while cutting tissue with the electrode to cause coagulation of the tissue simultaneously with the cutting.

In one embodiment, the controls comprise three buttons in the housing for allowing operating the device in the cut mode, the conventional coagulation mode, the argon plasma coagulation mode, and the plasma cut mode. In another embodiment, the controls comprise a footswitch for allowing operating the device in the cut mode, the conventional coagulation mode, the argon plasma coagulation mode, and the plasma cut mode. The simultaneously cutting and coagulating may cause a low depth of injury to the tissue. It may also cause a small diameter of injury to the tissue. The flow rate of the inert gas through the channel may be between 0.1 and 10 L/min.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 5E-F are tables of the numerical values corresponding to the graphs in FIGS. 5A-D.

FIGS. 8B-C are tables of the numerical values corresponding to the graph in FIG. 8A.

FIGS. 9E-F are tables of the numerical values corresponding to the graphs in FIGS. 9A-D.

FIG. 11C is a table of numerical values corresponding to the graphs in FIGS. 11A and 11B.

FIGS. 15A and 15B are a table and graph of argon plasma coagulation data with a USMI SS-200E/Argon 2 system.

FIGS. 16A and 16B are a table and graph of hybrid plasma cut data with a USMI SS-200E/Argon 2 system in hybrid plasma cut mode in accordance with a preferred embodiment of the present invention.

FIGS. 17A and 17B are a table and graph of hybrid plasma cut data with a USMI SS-601MCa/Argon 4 system in hybrid plasma cut mode in accordance with a preferred embodiment of the present invention.

FIG. 18A is a table of depth of injury data with a USMI SS-200E/Argon 2 system in conventional cut mode.

FIG. 18B is a table of depth of injury data with a USMI SS-200E/Argon 2 system in conventional coagulation mode.

FIG. 18C is a table of depth of injury data with a USMI SS-200E/Argon 2 system in argon coagulation mode.

FIG. 18D is a table of depth of injury data with a USMI SS-200E/Argon 2 system in hybrid plasma cut mode in accordance with a preferred embodiment of the present invention.

FIG. 18E is a table of depth of injury data with a USMI SS-601MCa/Argon 4 system in hybrid plasma cut mode in accordance with a preferred embodiment of the present invention.

DETAILED DESCRIPTION OF THE PREFERRED EMBODIMENTS

Figure 1A:
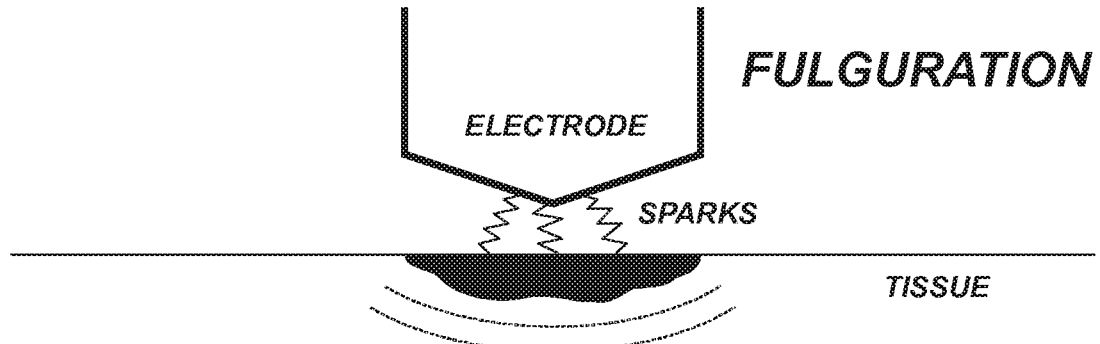
FIG. 1A is a diagram illustrating a conventional fulguration mode of operation of an electrosurgical device.
Figure 1B:
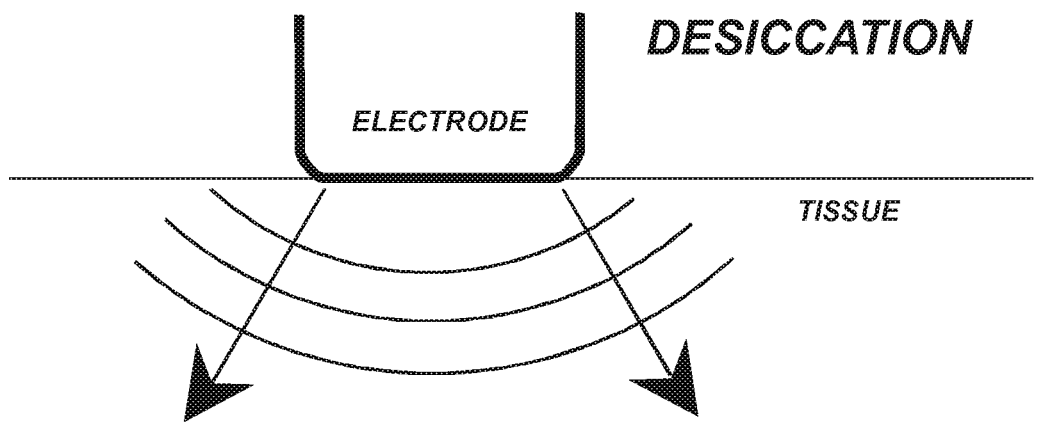
FIG. 1B is a diagram illustrating a conventional desiccation mode of operation of an electrosurgical device.
Figure 1C:
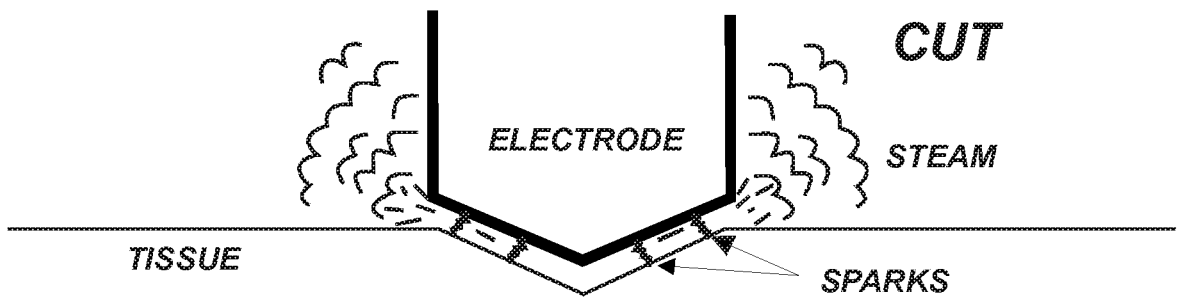
FIG. 1C is a diagram illustrating a conventional cutting mode of operation of an electrosurgical device.
Figure 2A:
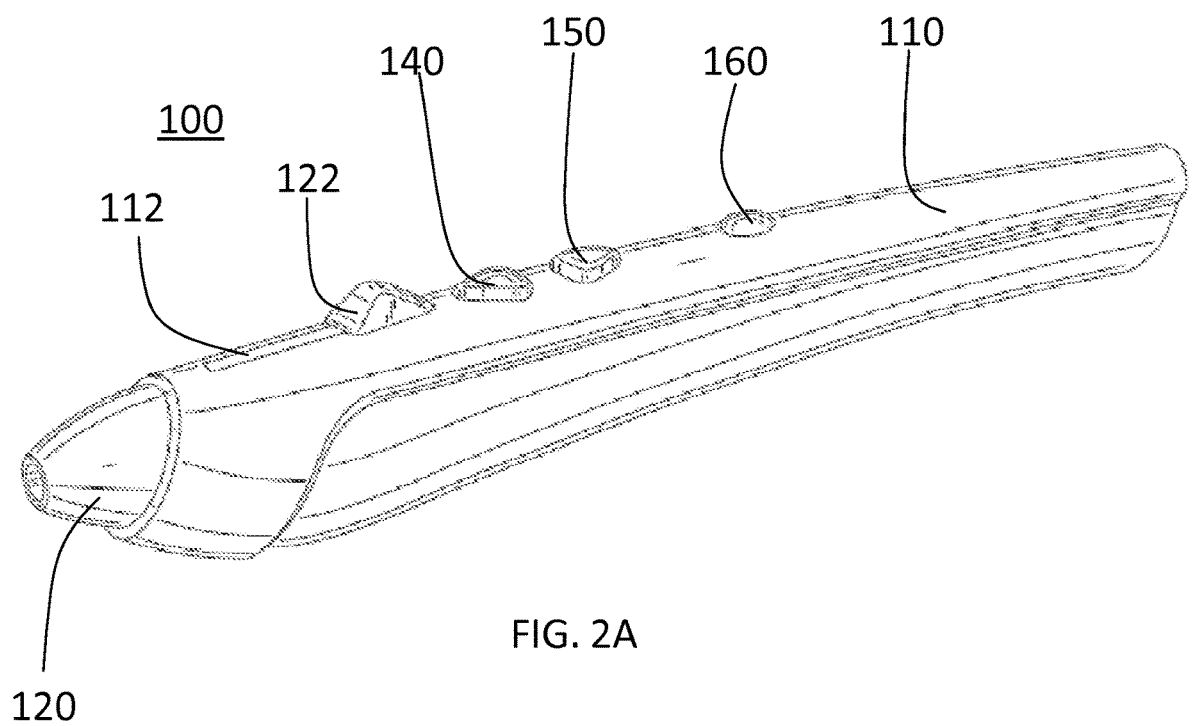
FIG. 2A is a perspective view of an electrosurgical handpiece having its electrode retracted within its housing in accordance with a first preferred embodiment of the present invention.
Figure 2B:
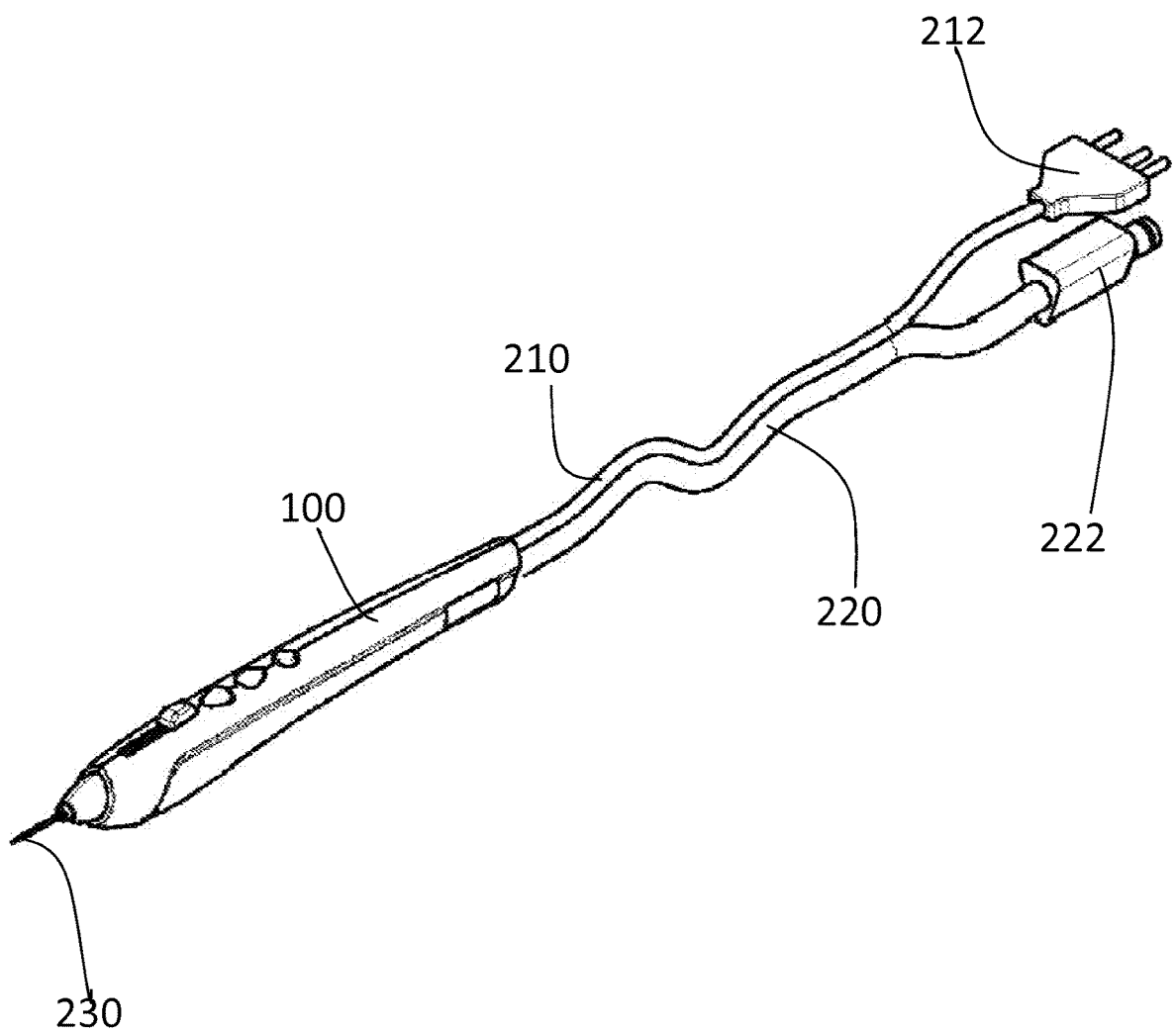
FIG. 2B is a perspective view of an electrosurgical handpiece having its electrode extending out from a distal end of its housing in accordance with a first preferred embodiment of the present invention.
Figure 2C:
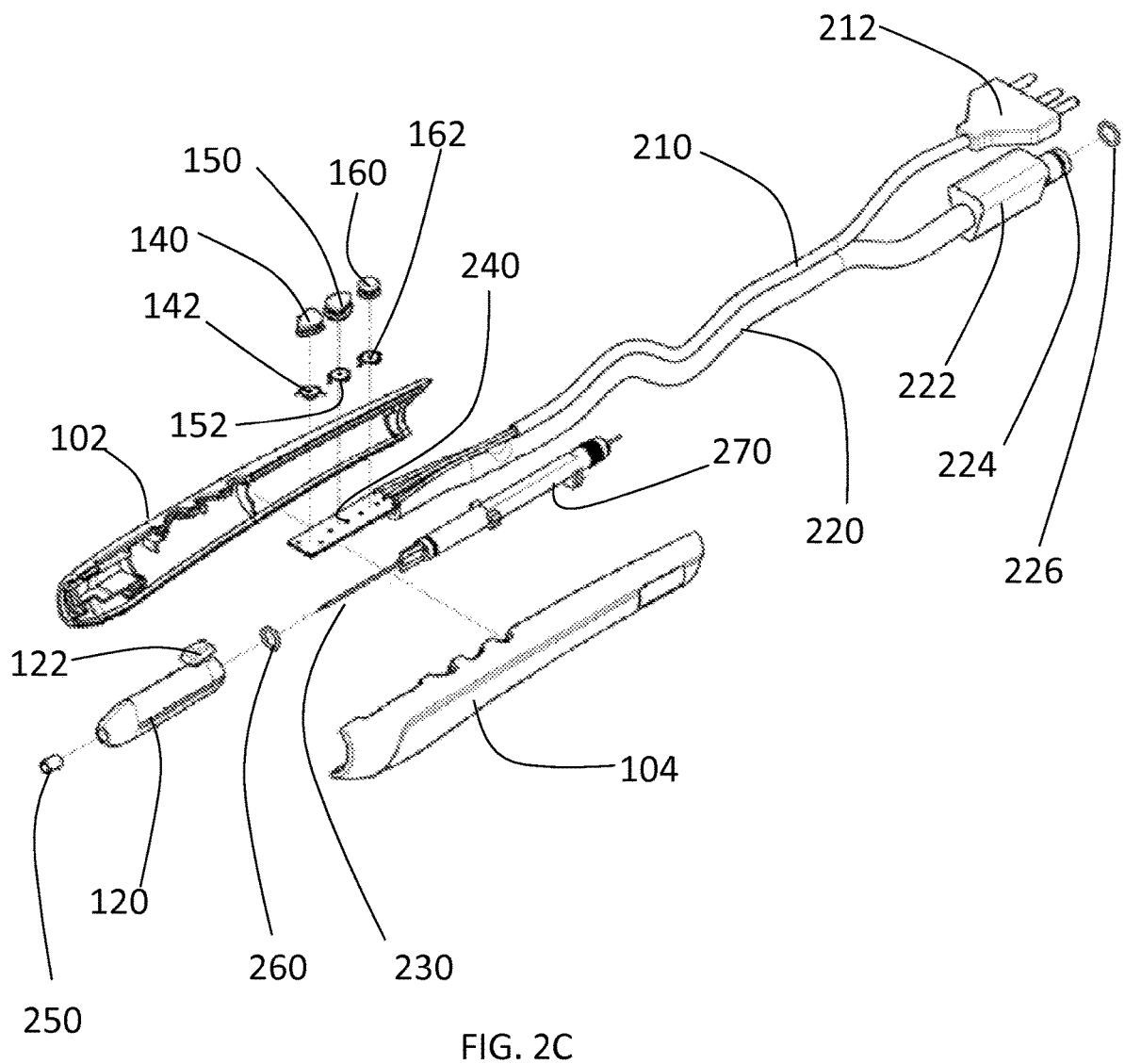
FIG. 2C is an assembly drawing of an electrosurgical handpiece in accordance with a first preferred embodiment of the present invention.

A preferred embodiment of an electrosurgical device 100 in accordance with the present invention is described with reference to FIGS. 2A-2C. The electrosurgical device, handpiece or pencil 100 has a rigid housing 110 and telescoping nozzle or tip 120. The rigid housing may be formed, for example, from molded sides 102 and 104. The two sides 102, 104 are joined to form housing 110 having a hollow chamber within. Within the housing 110 is an electrode 230, electrode tubing 270 and a fiberglass plate 240. The electrode 230 extends through the electrode tubing 270. The electrode tubing additionally has within it a channel, tube or other means for conducting the inert gas from the distal end of tubing 220 through the electrode tubing 270 and out of the electrode tubing 270. The inert gas leaving the channel in the electrode tubing then passes out of an opening at the distal end of the nozzle 120. The fiberglass plate 240 and electrode 230 are connected to electrical cable assembly 210. The electrode tubing is connected at its distal end to the hose tubing 220. An O-ring is placed between the telescoping nozzle and the electrode tubing to form a seal therebetween. A ceramic tip 250 may be placed at a distal end of the telescoping tip or nozzle 120 to protect the nozzle 120 from heat damage where the electrode passes through an opening at the distal end of the nozzle 120. The electrical cable assembly extends from a proximal end of the housing 110 and has at its distal end a plug 212. During operation of the device, the connector 212 is connected to an electrosurgical generator. The PVC hose tubing also extends from the proximal end of the housing 110 and has at its distal end a gas connector body 222, a gas connector tip 224 and an O-ring 226. During operation of the device, the gas connector assembly (222, 224, 226) is connected to a source of an inert gas such as argon.

The housing 110 has a plurality of opening or holes for accommodating a plurality of controls or buttons 140, 150, 160. The telescoping nozzle or tip 120 has a control element 122 extending through a slot 112 in the housing 110. The control element, tab, know or slider 122 is used by a surgeon to move the telescoping tip 120 into or out of an opening in a distal end of the housing 120. Three controls or buttons 140, 150, 160, extend out of openings in the housing 110 and have springs 152 between them and fiberglass plate or connected 240 to bias the controls or buttons away from the plate or connector 240.

The electrosurgical device of the present invention can be operated, for example, in four different modes: conventional cut mode, conventional coagulation mode, argon plasma coagulation mode, and hybrid plasma cut mode. The eschar resulting from cutting and coagulation in the hybrid plasma cut mode in accordance with the present invention is substantially better than conventional fulguration, cutting and argon plasma coagulation techniques. In addition, there is substantial absence of charring, carbonization, tissue necrosis and destruction of adjacent tissue. Thus, tissue can be precisely cut, and the adjacent vessels simultaneously sealed with minimal depth of injury, tissue necrosis, eschar and carbonization.

An inert gas combined with high-frequency energy in the plasma cut mode can precisely cut through tissues (i.e. skin, muscle, bone or vascular) with substantial speed and accuracy.

Any generator that provides high-frequency voltage to ionize the inert gas to form a gas stream can be used. Preferred generators include the Canady Plasma™ Electrosurgery Unit model (SS-601 MCa) and the Canady Plasma™ Electrosurgery Unit model (SS-200E) that are preferably used with the Argon plasma units Canady Plasma™ Argon 4 Coagulator (CPC 4) and Canady Plasma™ Argon 2 Coagulator (CPC 2), respectively. The CPC 4 provides a controlled flow of inert gas to the electrosurgical device during argon plasma coagulation mode and in hybrid plasma cut mode. The flow rate and the power can be manually set. In a coagulation mode, the generator delivers, for example, a peak-to-peak voltage of less than 9000 volts. In a cut mode, for example, the generator delivers a peak-to-peak voltage of less than 3800 volts. Most preferably, a peak-to-peak voltage of 100 to 9000 volts is delivered by the generator.

Any accessory devices can be attached to the electrosurgery unit/plasma unit combination. Exemplary devices are an electrosurgical device (a handpiece) or an argon plasma flexible probe (catheter), rigid or laparoscopic.

For operating the electrosurgical device, high-frequency current can be activated by two push buttons for the conventional cut mode and the conventional coagulation mode, respectively. Argon gas may be delivered by activating a third push button. This activation will allow the argon plasma coagulation mode and the hybrid plasma cut mode. The plasma cut mode will cut and coagulate the tissue at the same time. It can be easily switched between the different modes by activating the respective buttons. The plasma or electrical current can also be activated by a footswitch.

The telescoping nozzle of the electrosurgical device can be extended or shortened over the electrode as desired when performing plasma procedures. In a preferred embodiment, the electrode extends 2 to 25 mm outside the telescoping nozzle.

The electrode can be of any common material of the state of the art. In a preferred embodiment, the electrode is a tungsten wire.

In a preferred embodiment, the present invention is an electrosurgical method for achieving cutting and coagulating simultaneously with a source of inert, ionizable gas in combination with high-frequency energy. The source of inert, ionizable gas can be any kind of inert, ionizable gas. The preferred type of gas for use in cutting is pure argon. Argon gas causes a decrease in tissue temperature which limits micro-destruction of tissue, improves through conductivity of tissue and allows high-frequency cutting through tissue at low tissue temperatures. Inert gas also dissipates oxygen molecules from the surgical area and prevents oxidation of tissue which causes decrease local tissue temperature and prevents carbonization. Flow rates can vary and can be adjusted depending on the tissue that is being cut.

A high-frequency current supplied by an electrosurgical generator is transmitted through an electrode. Electrodes can be composed, for example, of tungsten, stainless steel, ceramic or any electrical conducting material. An electrical discharge is created between the active electrode and the tissue. The discharge is ignited by AC voltage with a typical amplitude and frequency at 4 kV and or greater than 350 kHz respectively. The voltage waveform preferably is a sinusoidal waveform that contains alternate positive and negative sections of approximately equal amplitudes. An inert gas flows through the channel containing the electrode. The electrode contacts the tissue and delivers an ionized plasma high-frequency current through the tissue. A new phenomenon has been created by the present invention, which can precisely cut through the tissue and simultaneously seal adjacent vessels and tissue with.

The present invention is further evidenced by the following examples.

Ex Vivo Porcine Model

All ex vivo porcine experiments were carried out on explant porcine liver samples @Micropropulsion and Nanotechnology Laboratory (MpNL), George Washington University, Washington, D.C and WEM Equipamentos Plasma Research Laboratory, Ribeirao Preto—Sao Paulo, Brazil. Liver samples were immediately placed in 10% formalin solution ph 7.0 and sent for H & E preparation of the pathological slides and interpretation at Laboratorio de Patologia Cirurgica Dr Prates, Ribeirao Preto—Sao Paulo, Brazil In Vivo Porcine Model In vivo porcine surgical operations were performed at the University of Sao Paulo, Department of Surgery and Anatomy, Animal Research Laboratory, Ribeirao Preto, SP, Brazil. Approval was obtained by the institution animal research director. Three dalland female swine (mean weight 14.5 kg) were used in this study. Anesthesia was induced with ketamine 50 mg/cc mixed and dopaser-xilazina 200 mg/10 cc, intramuscular. Animals were then intubated, and anesthesia was maintained with Na Pentathol to effect. The skin was prepped with alcohol and draped in the usual sterile manner. Mercedes, abdominal midline, and median sternotomy were made during the operations with the plasma scalpel. Multiple surgical procedures were performed median sternotomy, gastric resection, partial splenectomy, partial nephrectomy, partial hepatectomy, wedge resection of the liver, intestinal resection and skin incisions. Operations were video-recorded. Observations of surgical bleeding during the procedure were recorded. Depth of injury and eschar was compared with four high frequency operations modes: conventional cut and coagulation, argon plasma coagulation and hybrid argon plasma cut. Samples of the skin, liver, stomach, intestine, and bone were placed in 10% formalin solution ph 7.0 and sent for H & E preparation of the pathological slides and measurement of depth of injury and diameter of eschar at Laboratorio de Patologia Cirurgica Dr Prates, Ribeirao Preto—Sao Paulo, Brazil. Animals were sacrificed by using an intravenous injection of pentobarbital sodium and phenytoin sodium.

The hybrid plasma scalpel blade of the present invention was used in combination with USMI's SS-200E/Argon 2 and SS-601MCa/Argon 4 to evaluate in four high frequency operation modes: (i) conventional cut; (ii) conventional coagulation; (iii) conventional argon plasma coagulation (APC); and (iv) hybrid plasma cut. As described above in the background of the invention, conventional cut and coagulation modes do not involve the use of an inert gas such as argon. Instead, they are performed by touching the target tissue with the active electrode. Conventional argon plasma coagulation is performed as it was described above in the background of the invention. The hybrid plasma cut mode is the mode of the present invention described above in the detailed description of the preferred embodiments. The hybrid plasma scalpel used in all four modes is as described above with respect to FIGS. 2-C.

Four parameters were measured: plasma discharge column length, tissue heating, diameter of eschar and depth of injury by high frequency operation mode. The length of the plasma was characterized by the maximal length of the discharge plasma column observed at tissue treatment with the hybrid plasma scalpel at which the discharge can be sustained. The treatments were video-recorded by digital camera Nikon Coolpix 995 (15 frames/s) and the maximal length of discharge plasma column (L) was measured by post-experiment evaluation of recorded videos. The tissue heating was characterized by the temperature growth ($\Delta T$) of pig's liver sample appeared as result of application of hybrid plasma scalpel. $\Delta T$ was measured using the thermocouple (Type K) probes embedded in the pig's liver. The accuracy of temperature and length measurements were 5° C. and 0.5 mm respectively. Tissue temperature prior to treatment was 18-20° C. Eschar diameter produce by the plasma scalpel blade was measured using a digital caliber. Pathologists used an Motim Camera 1000, 1.3 an Olympus Microscope Bx 41 to calculate the depth of injury.

Figure 3A:
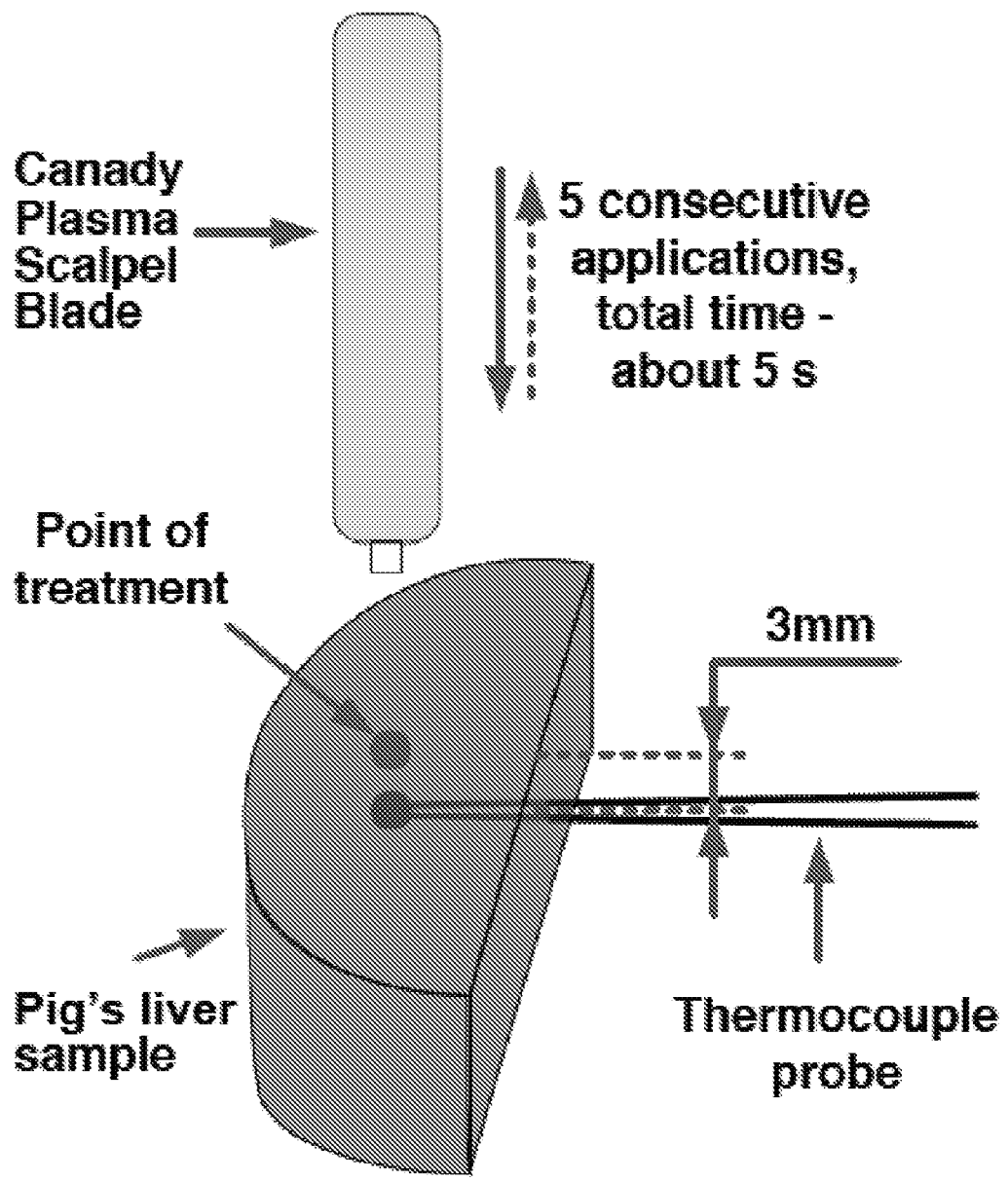
FIG. 3A is a diagram illustrating an experimental setup for testing in argon coagulation mode.
Figure 3B:
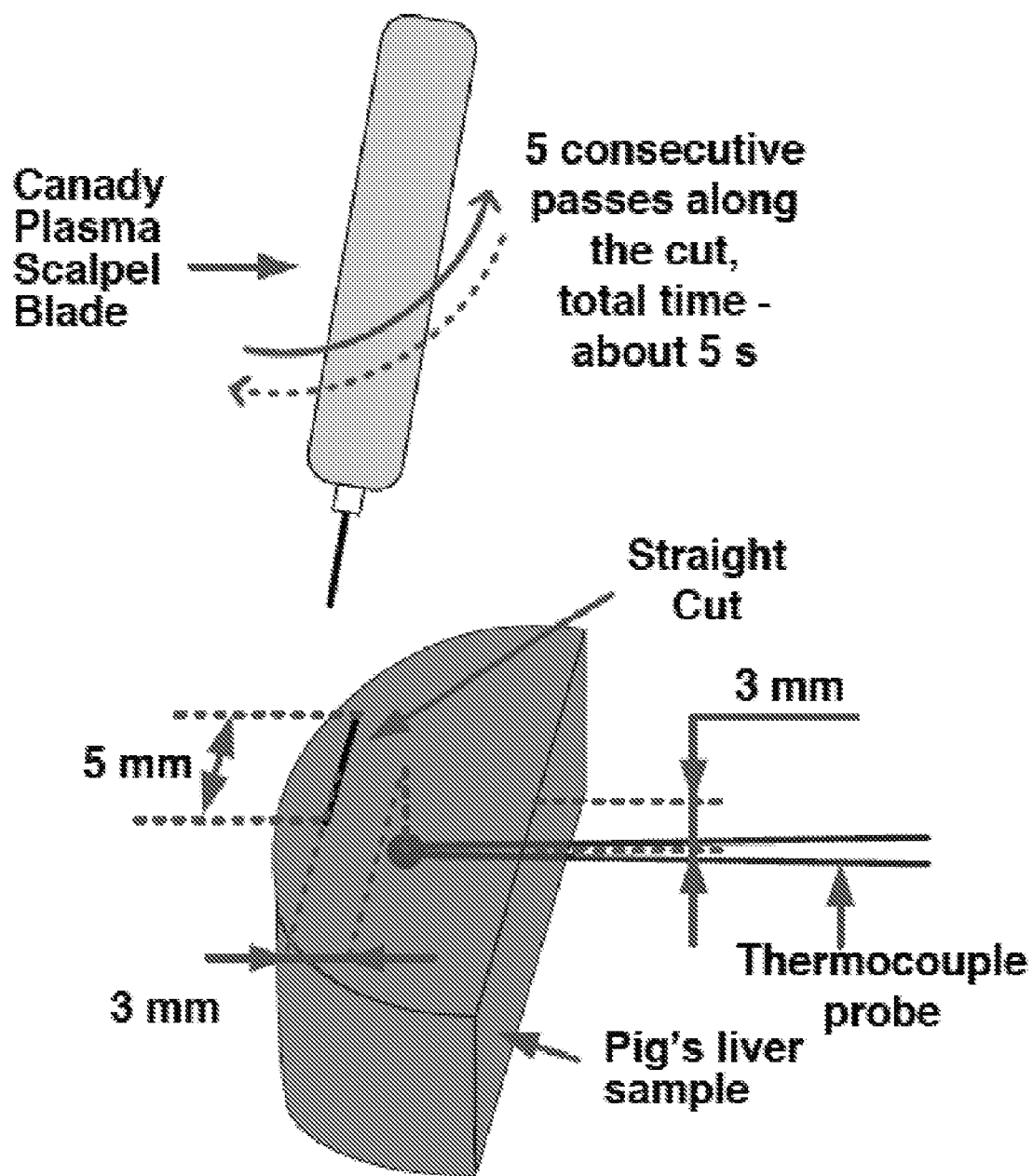
FIG. 3B is a diagram illustrating an experimental setup for testing a preferred embodiment of the present invention in hybrid plasma cut mode.
Figures 4A, 4B, 4C:
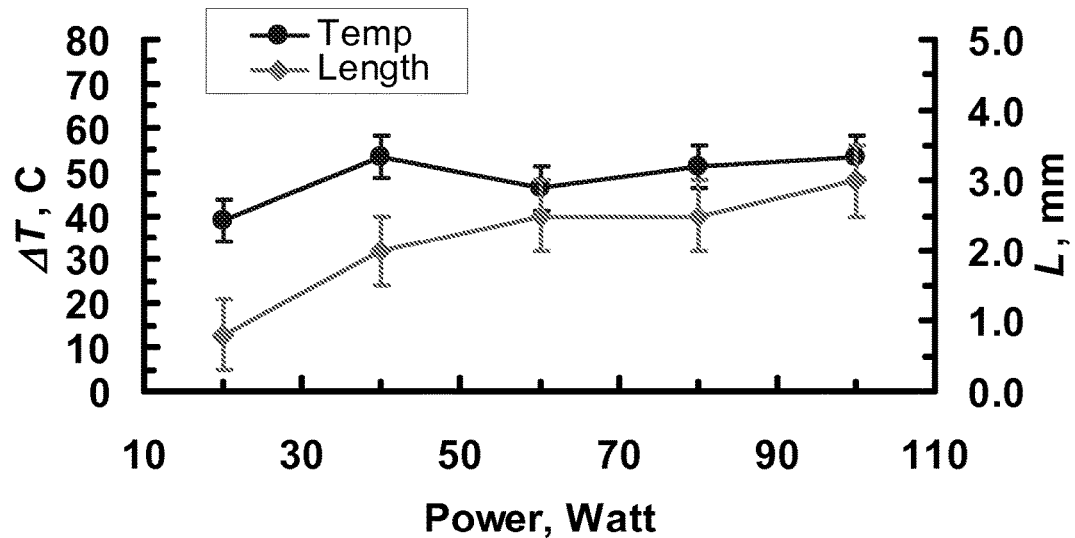
FIG. 4A is a graph of pig's liver sample temperature and spark length as function of power with a USMI SS-200E/Argon 2 system in conventional coagulation mode.
FIGS. 4B-C are tables of the numerical values corresponding to the graph in FIG. 4A.
Figure 5A:
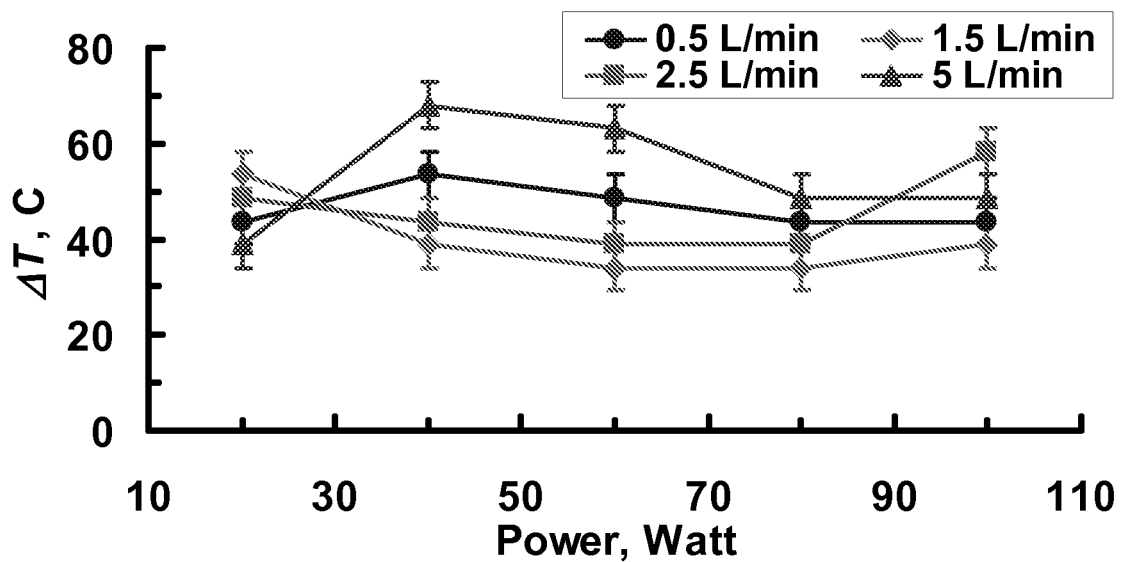
FIG. 5A is a graph of pig's liver sample temperature as function of power at various argon flow rate settings with a USMI SS-200E/Argon 2 system in argon plasma coagulation mode.
Figure 5B:
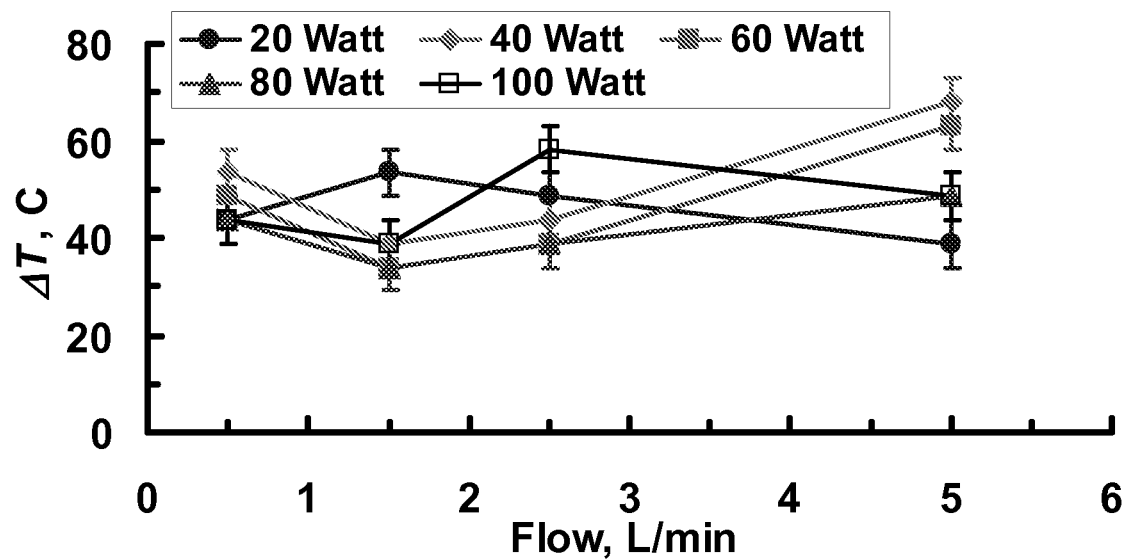
FIG. 5B is a graph of pig's liver sample temperature as function of argon flow rate at various power settings with a USMI SS-200E/Argon 2 system in argon plasma coagulation mode.
Figure 5C:
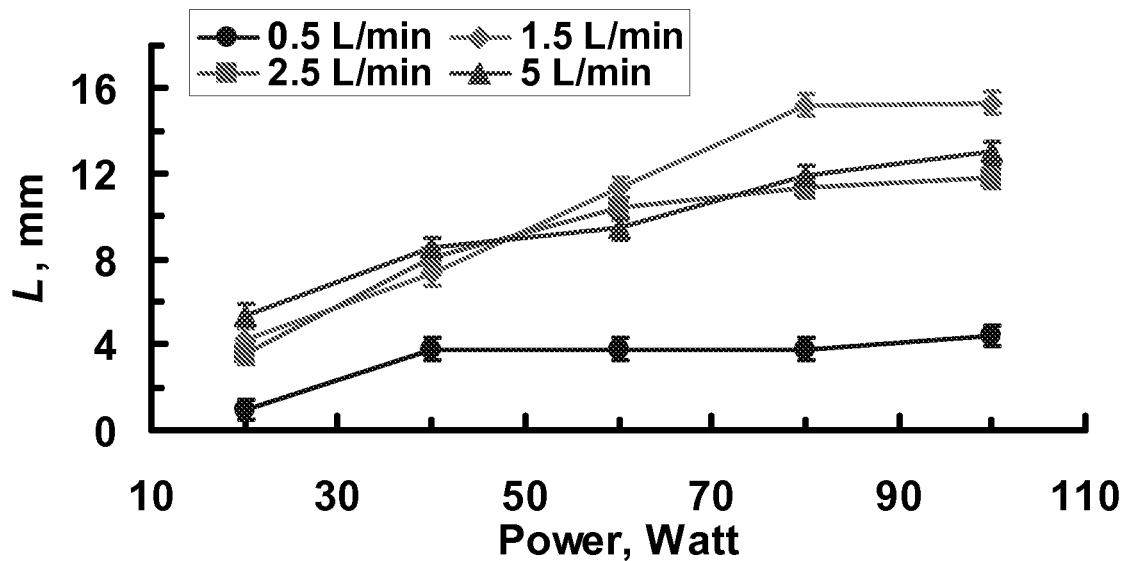
FIG. 5C is a graph of argon beam length as function of power at various argon flow rate settings with a USMI SS-200E/Argon 2 system in argon plasma coagulation mode.
Figure 5D:
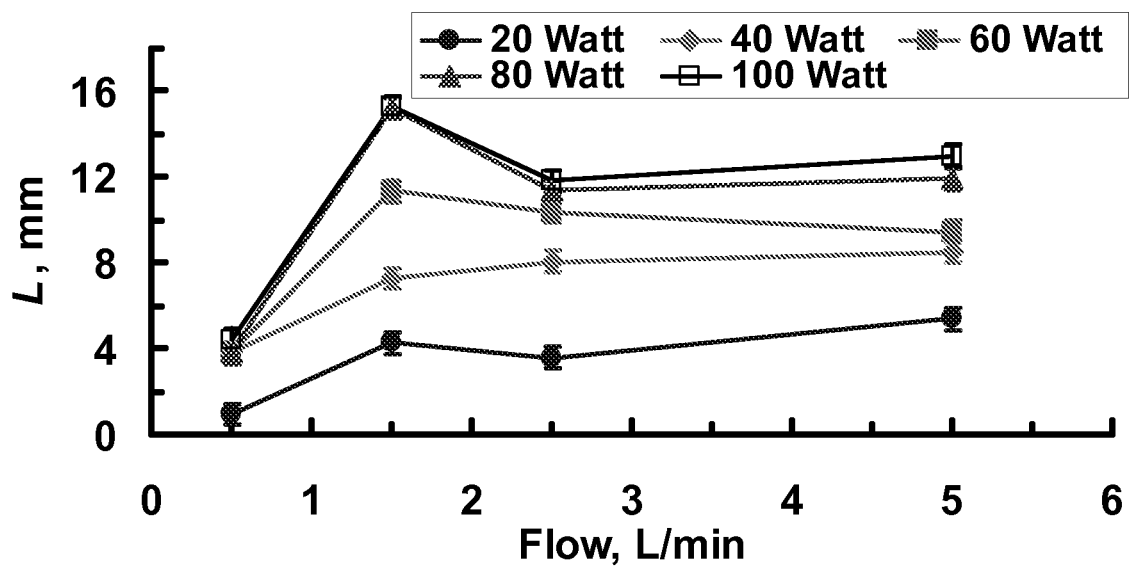
FIG. 5D is a graph of argon beam length as function of argon flow rate at various power settings with a USMI SS-200E/Argon 2 system in argon plasma coagulation mode.
Figures 6A, 6B:
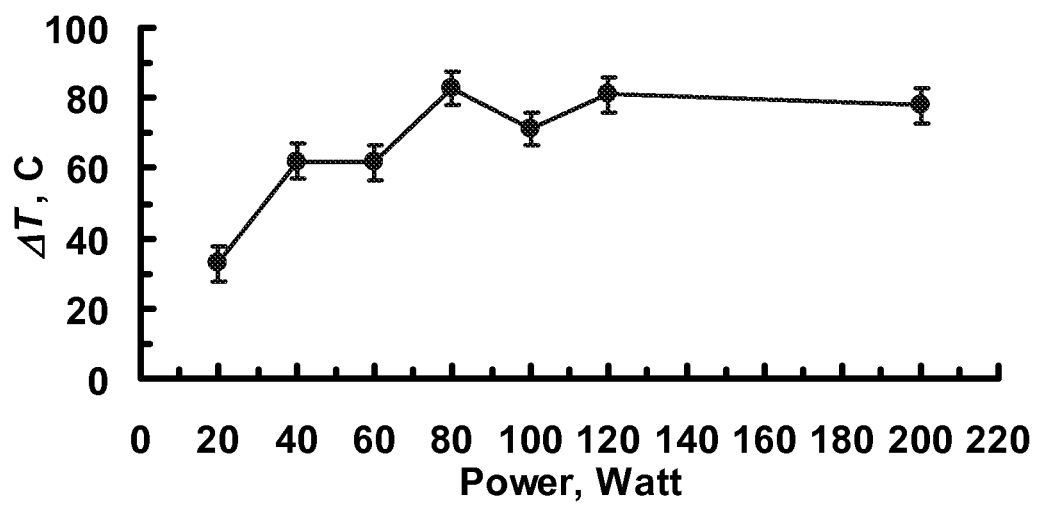
FIG. 6A is a graph of pig's liver sample temperature as function of power performed with a USMI SS-200E/Argon 2 system in conventional cut mode.
FIG. 6B is a table of the numerical values corresponding to the graph in FIG. 6A.
Figure 7A:
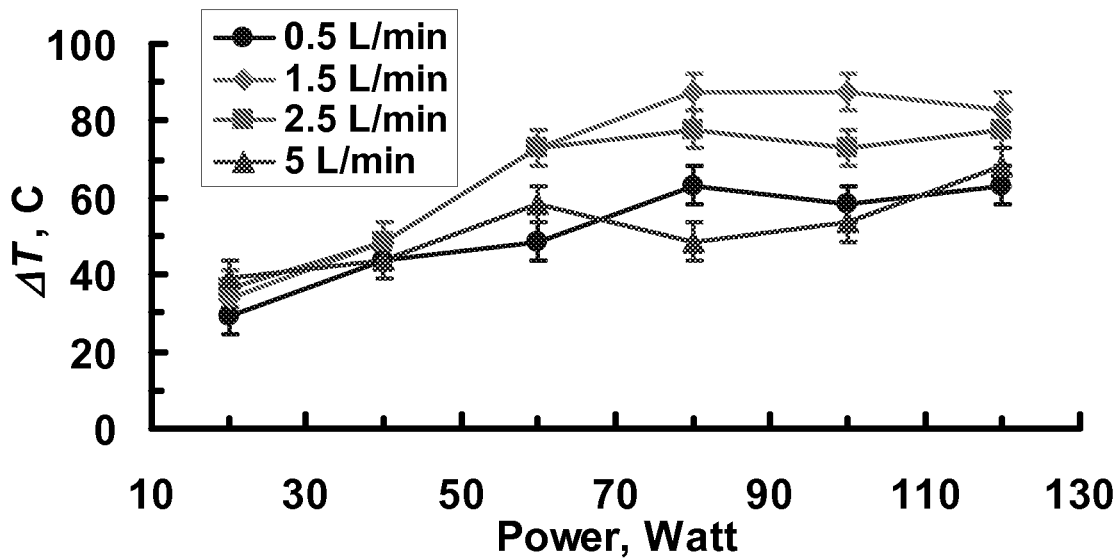
FIG. 7A is a graph of pig's liver sample temperature as a function of power at various flow rates performed with a USMI SS-200E/Argon 2 system in hybrid plasma cut mode in accordance with the present invention.
Figure 7B:
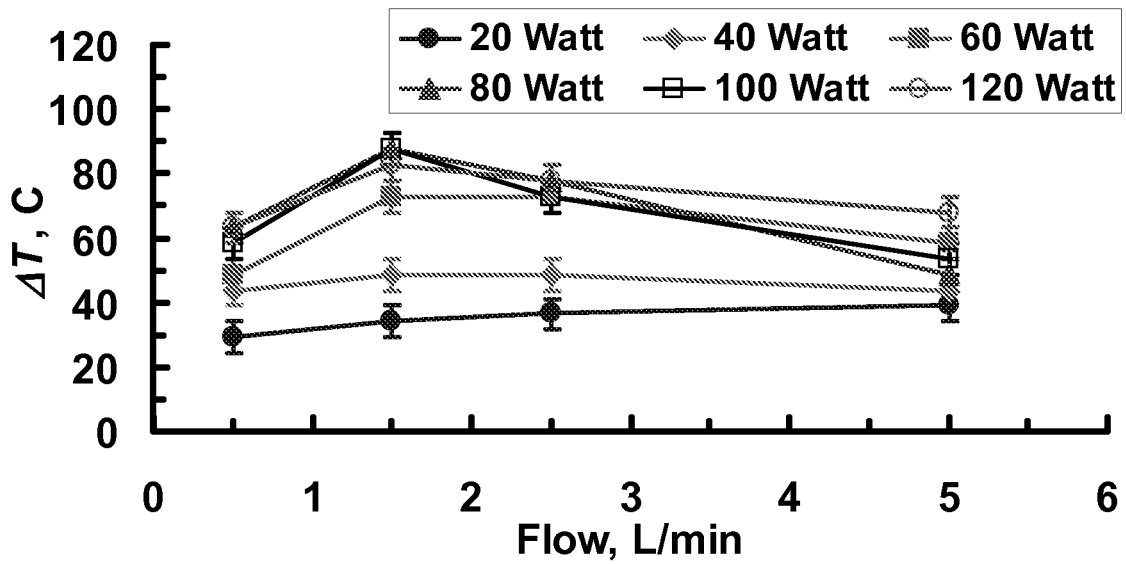
FIG. 7B is a graph of pig's liver sample temperature as a function of gas flow rate at various power settings performed with a USMI SS-200E/Argon 2 system in hybrid plasma cut mode in accordance with the present invention.
Figures 7C, 8A:
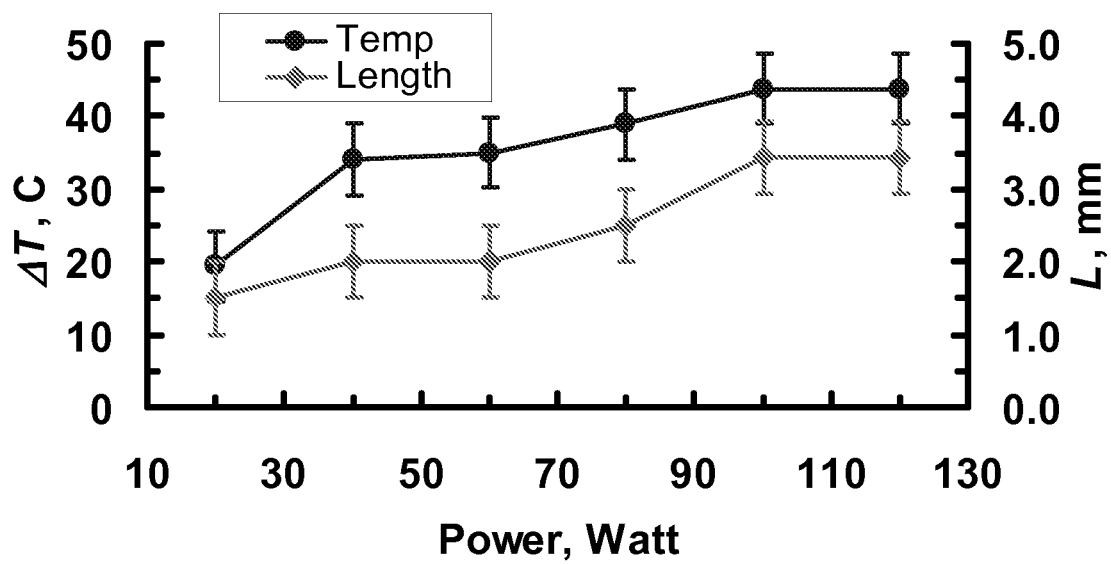
FIG. 7C is a table of numerical values corresponding to the graphs in FIGS. 7A and 7B.
FIG. 8A is a graph of pig's liver sample temperature and spark length as function of power with a USMI SS-601MCa/Argon 4 system in conventional coagulation mode.
Figure 9A:
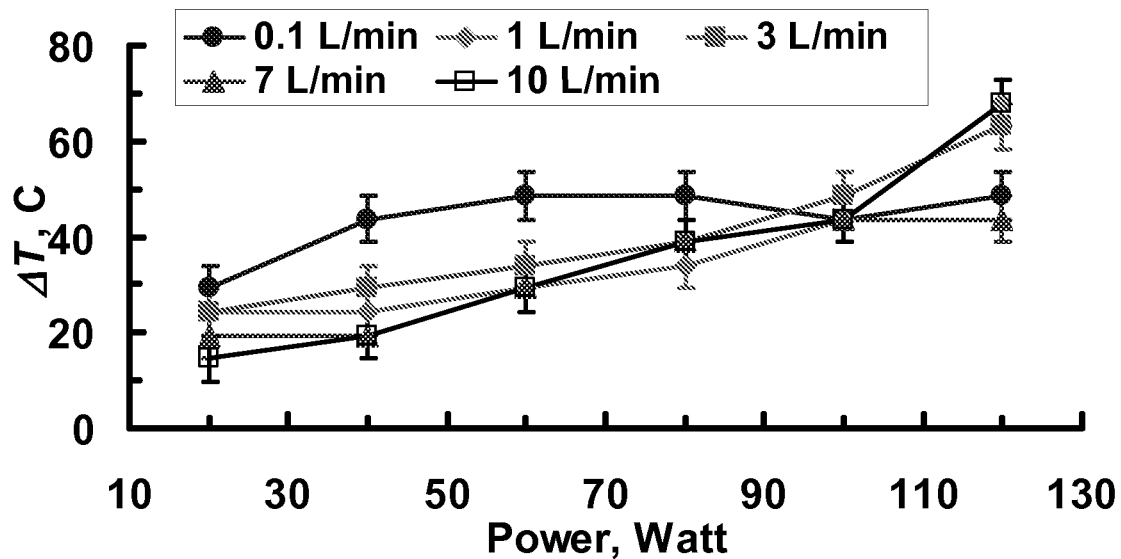
FIG. 9A is a graph of pig's liver sample temperature as function of power at various argon flow rate settings with a USMI SS-601MCa/Argon 4 system in argon plasma coagulation mode.
Figure 9B:
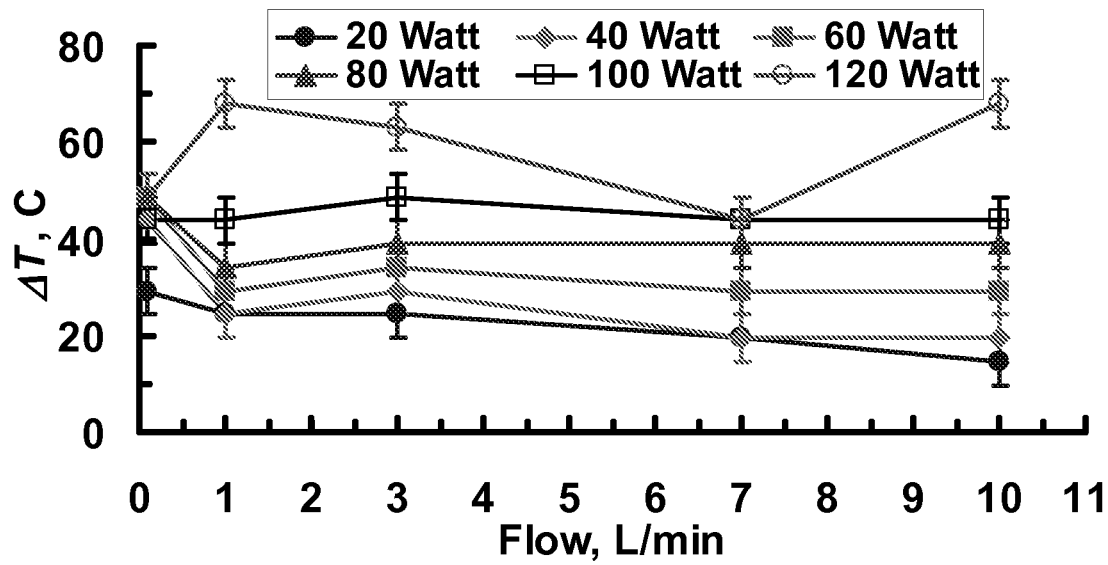
FIG. 9B is a graph of pig's liver sample temperature as function of argon flow rate at various power settings with a USMI SS-601MCa/Argon 4 system in argon plasma coagulation mode.
Figure 9C:
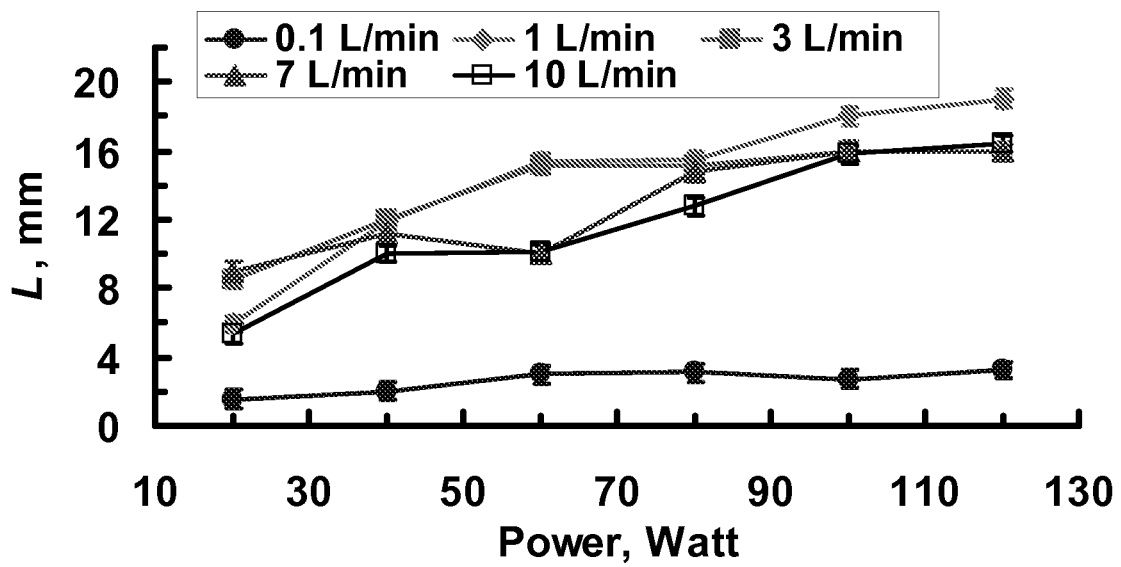
FIG. 9C is a graph of argon beam length as function of power at various argon flow rate settings with a USMI SS-601MCa/Argon 4 system in argon plasma coagulation mode.
Figure 9D:
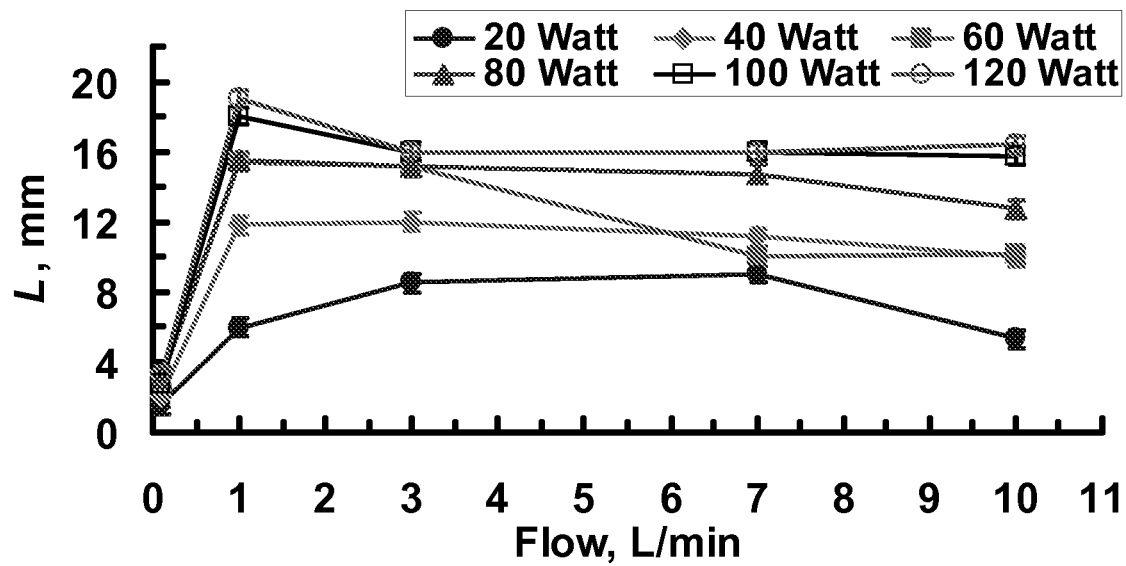
FIG. 9D is a graph of argon beam length as function of argon flow rate at various power settings with a USMI SS-601MCa/Argon 4 system in argon plasma coagulation mode.
Figures 10A, 10B:
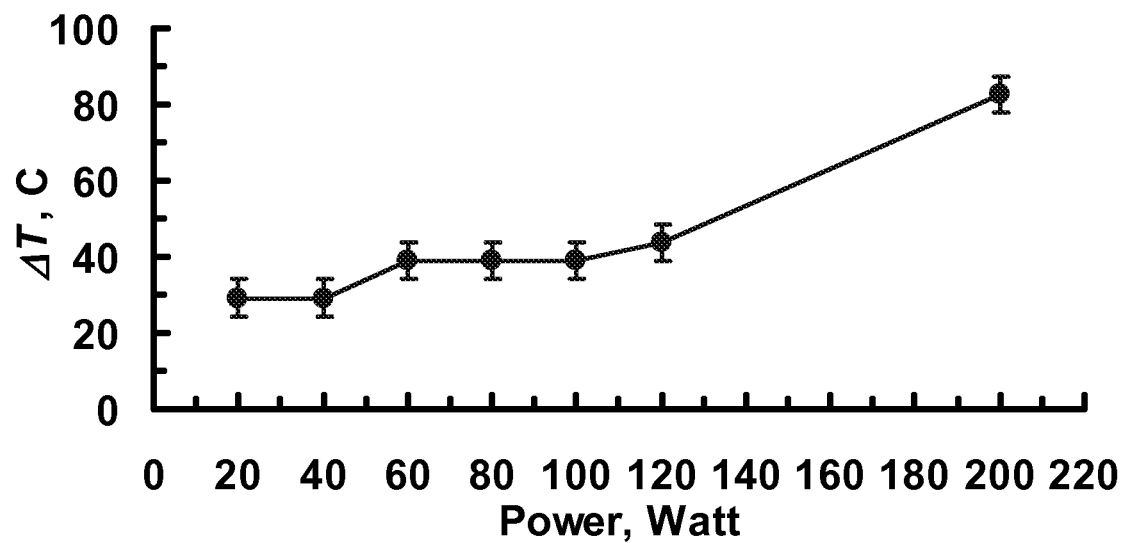
FIG. 10A is a graph of pig's liver sample temperature as function of power performed with a USMI SS-601MCa/Argon 4 system in conventional cut mode.
FIG. 10B is a table of the numerical values corresponding to the graph in FIG. 10A.
Figure 11A:
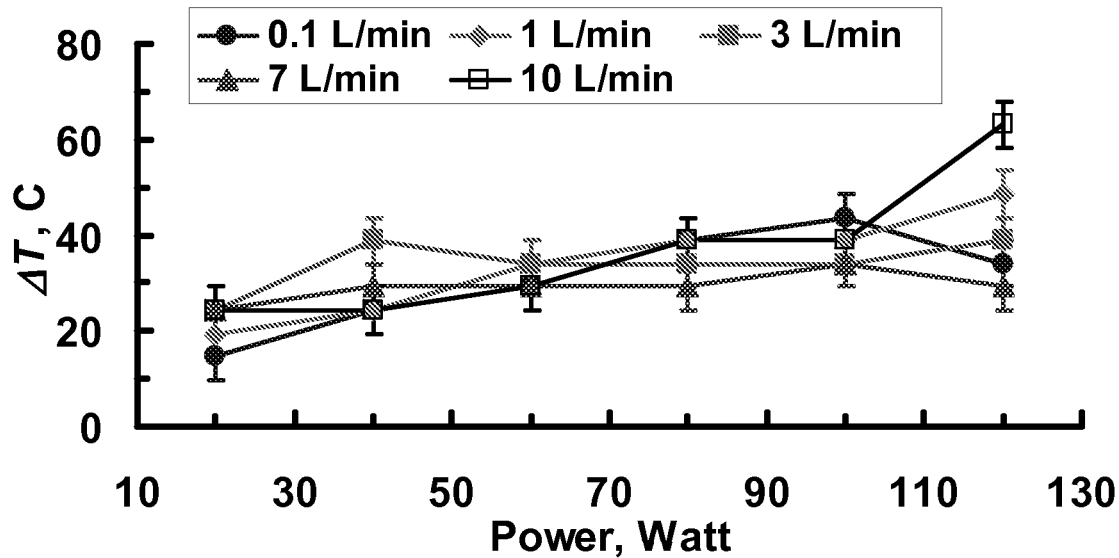
FIG. 11A is a graph of pig's liver sample temperature as a function of power at various flow rates performed with a USMI SS-601MCa/Argon 4 system in hybrid plasma cut mode in accordance with the present invention.
Figure 11B:
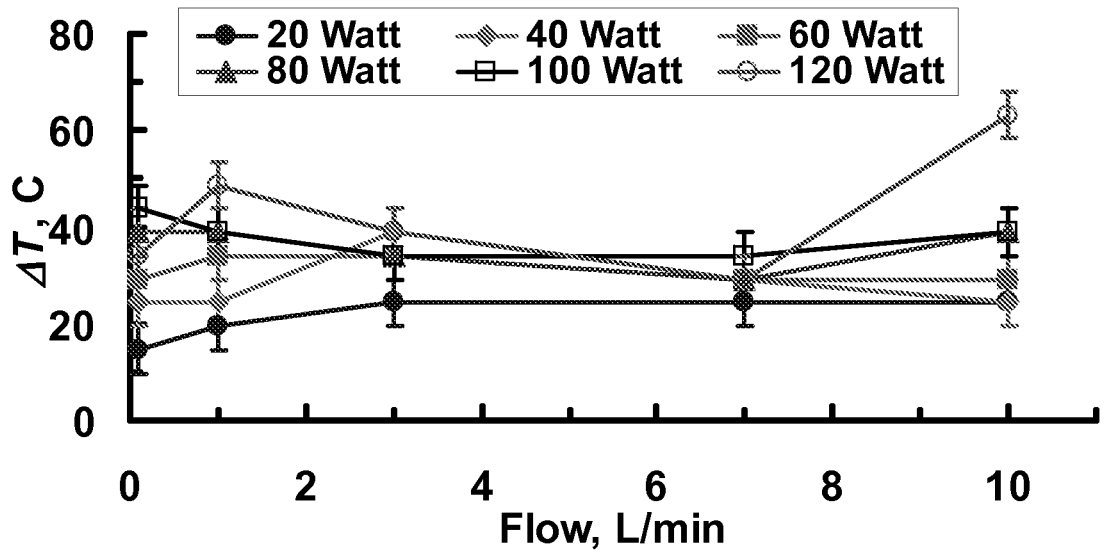
FIG. 11B is a graph of pig's liver sample temperature as a function of gas flow rate at various power settings performed with a USMI SS-601MCa/Argon 4 system in hybrid plasma cut mode in accordance with the present invention.
Figure 12A:
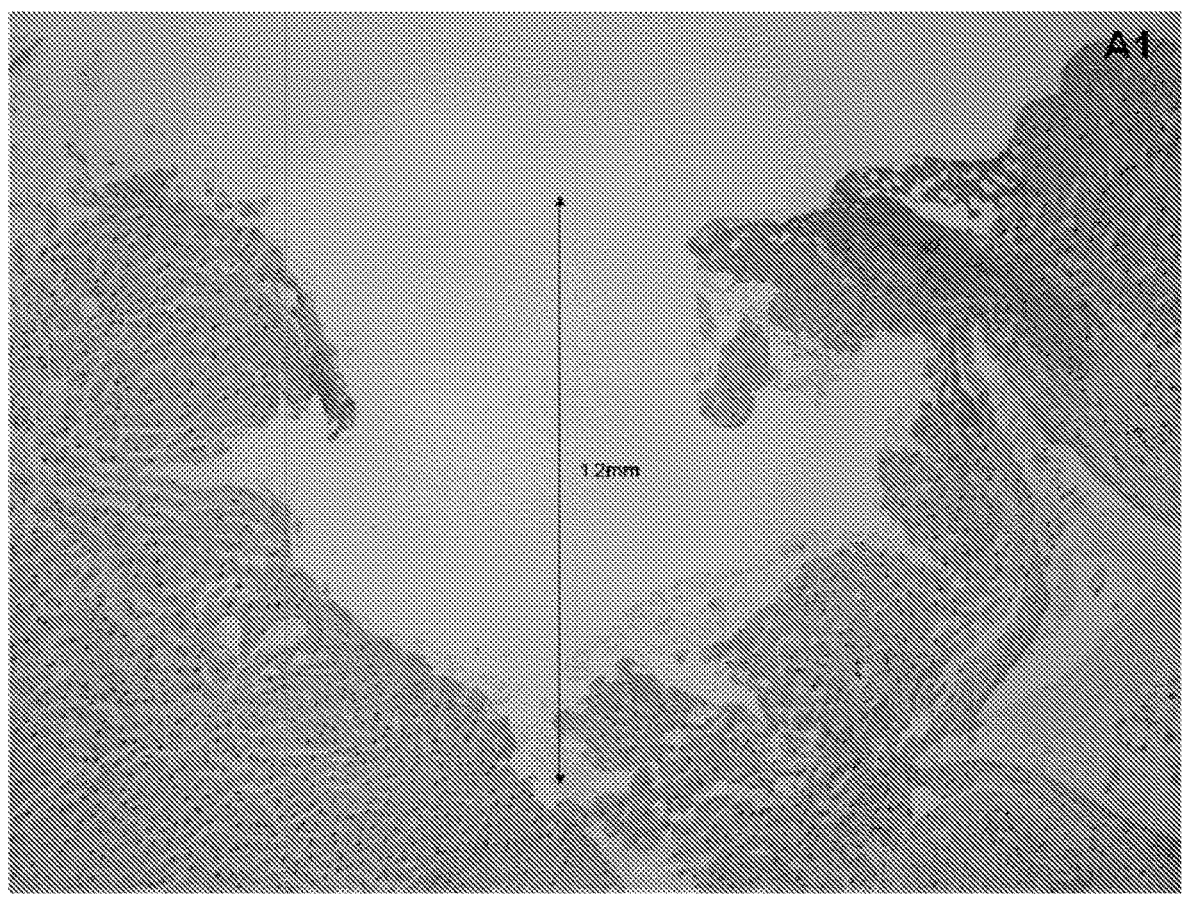
FIG. 12A is a tissue image illustrating depth of injury of 1.2 mm at a power setting of 20 W with a USMI SS-200E/Argon 2 system in conventional cut mode.
Figure 12B:
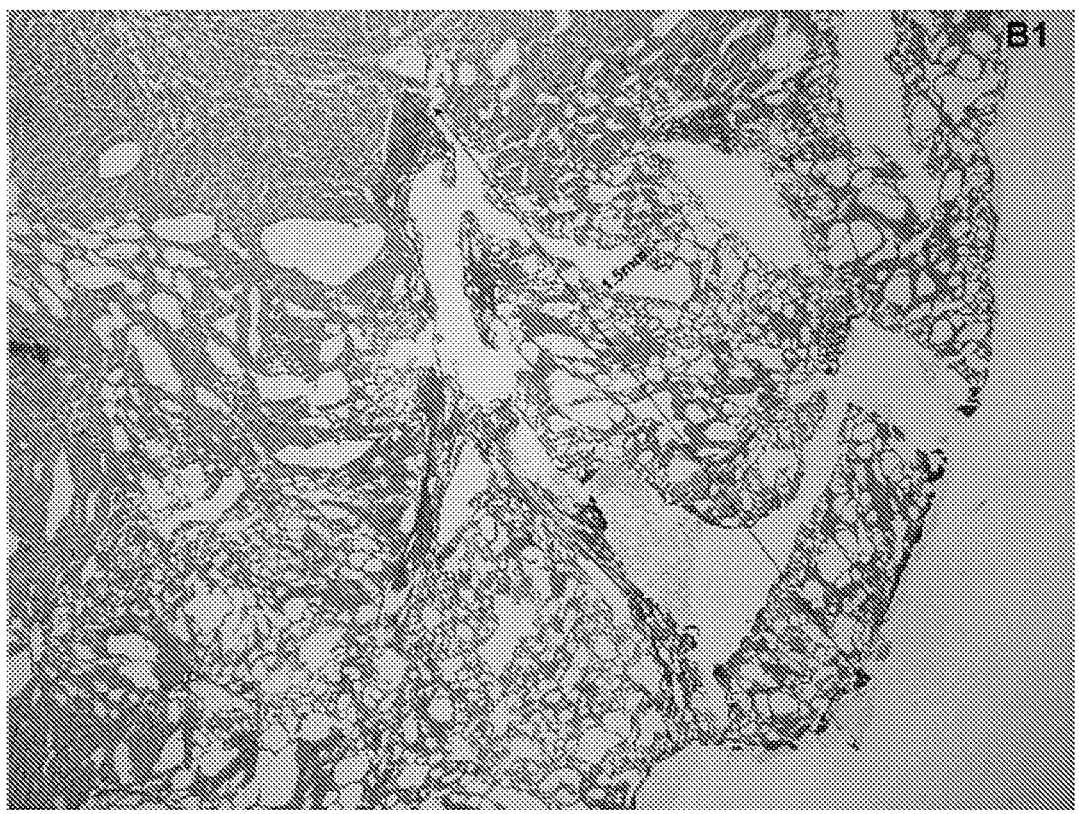
FIG. 12B is a tissue image illustrating depth of injury of 1.5 mm at a power setting of 20 W with a USMI SS-200E/Argon 2 system in conventional coagulation mode.
Figure 12C:
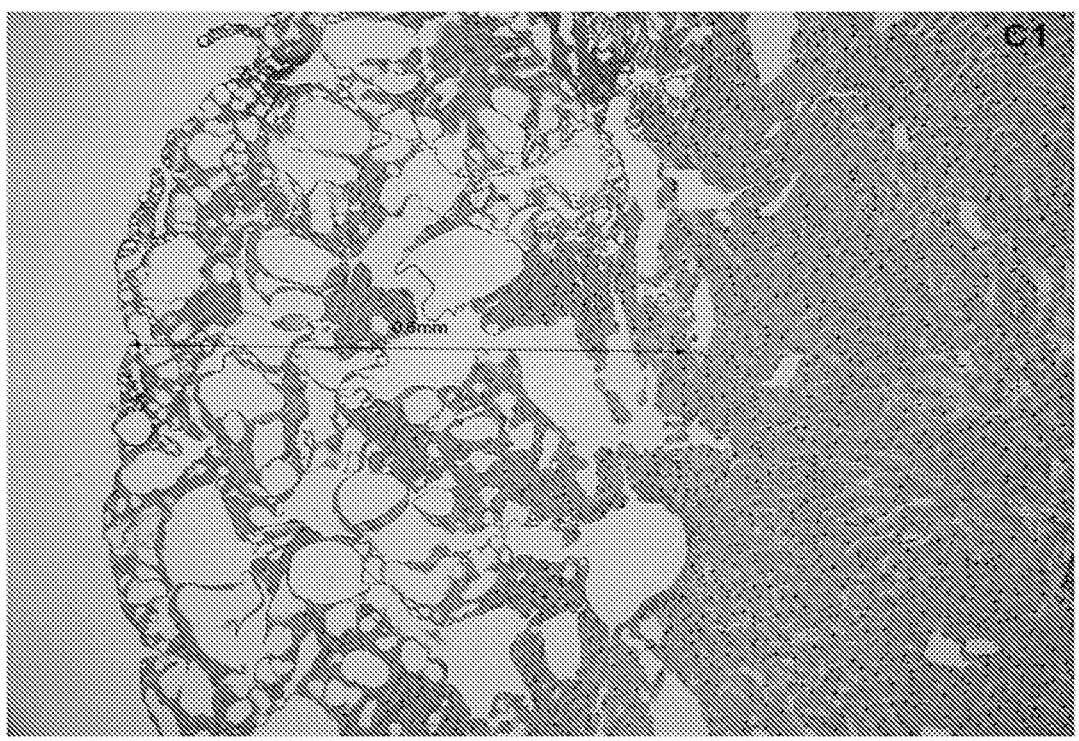
FIG. 12C is a tissue image illustrating depth of injury of 0.1 mm at a power setting of 20 W and a flow setting of 0.1 l/min. with a USMI SS-200E/Argon 2 system in hybrid plasma cut mode.
Figure 12D:
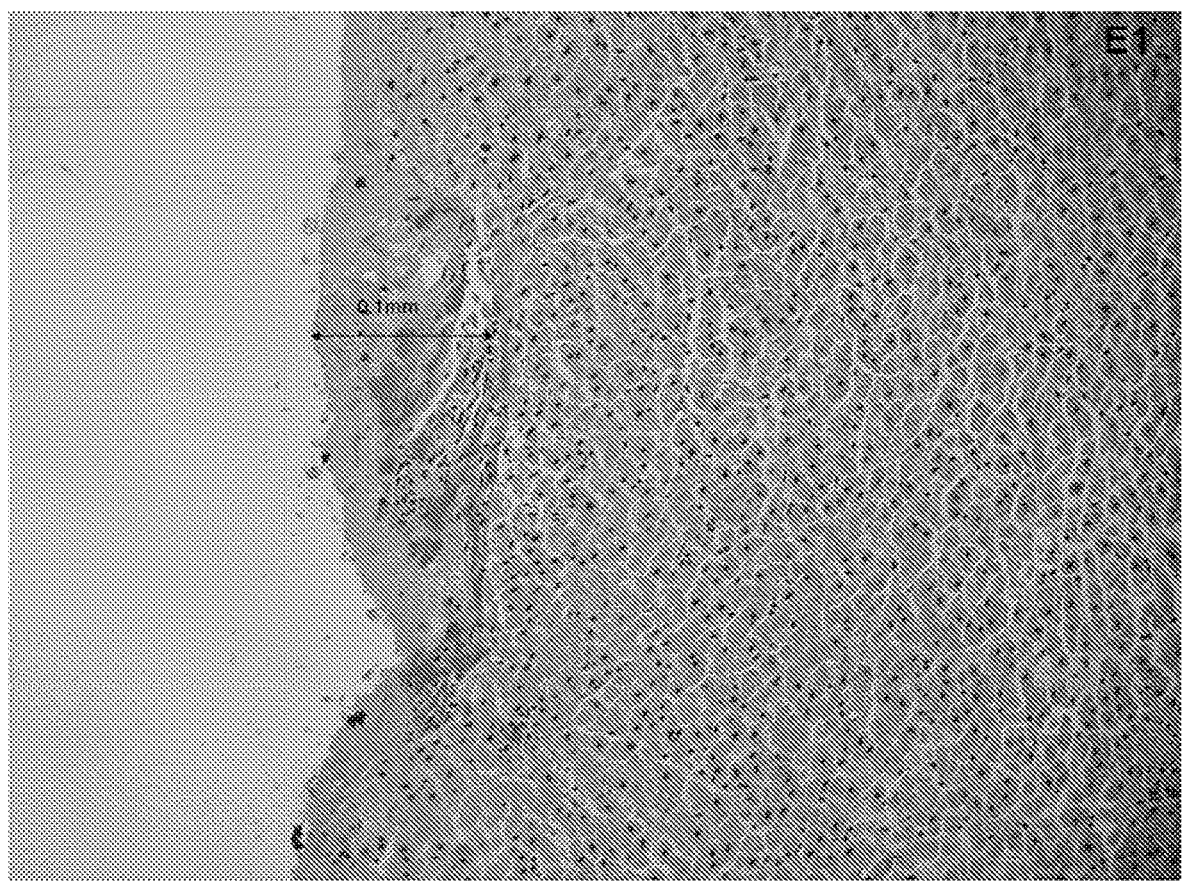
FIG. 12D is a tissue image illustrating depth of injury of 0.6 mm at a power setting of 20 W a flow setting of 0.5 l/min. with a USMI SS-200E/Argon 2 system in argon plasma coagulation mode.
Figures 13A, 13B:
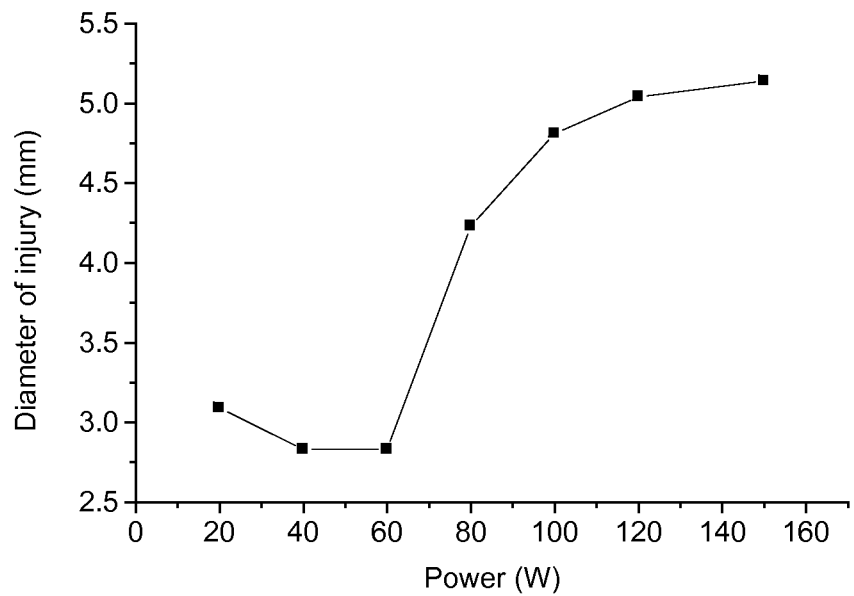
FIGS. 13A and 13B are a table and graph of conventional cut data with a USMI SS-200E/Argon 2 system.
Figures 14A, 14B:
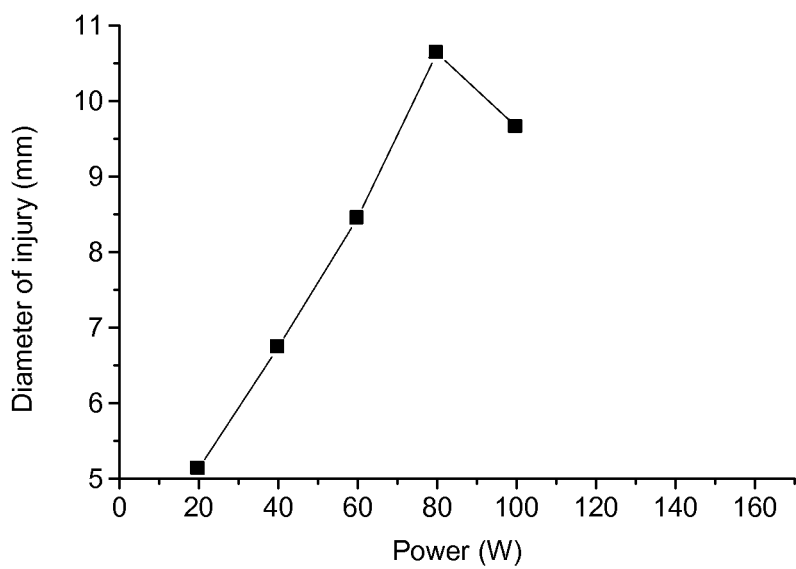
FIGS. 14A and 14B are a table and graph of conventional coagulation data with a USMI SS-200E/Argon 2 system.
Figure 15B:
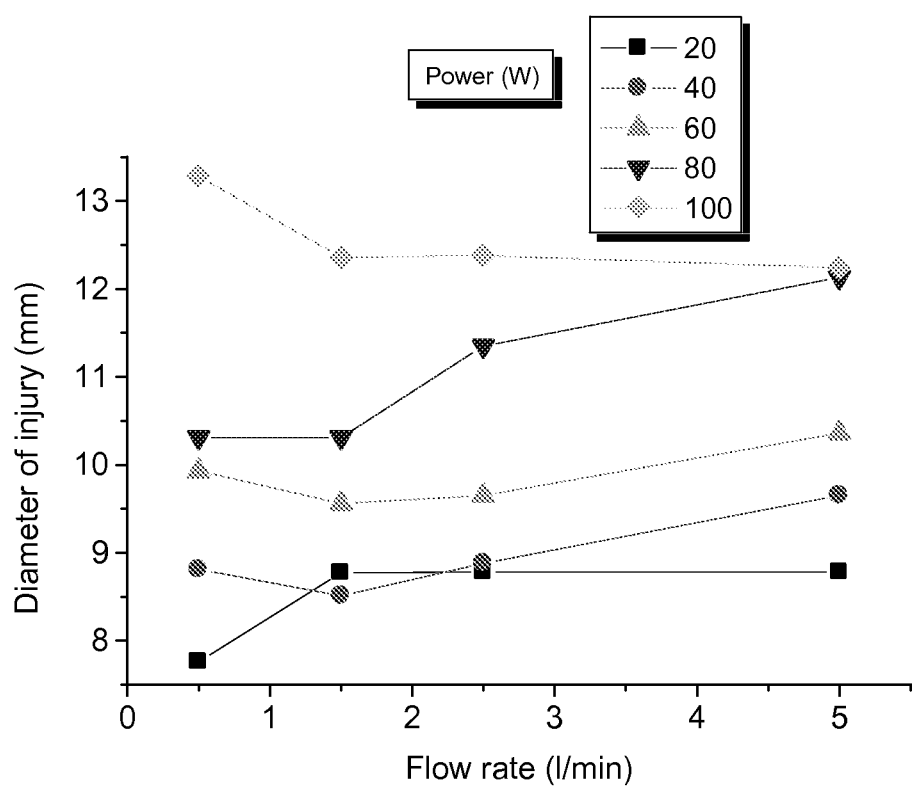
Figure 16B:
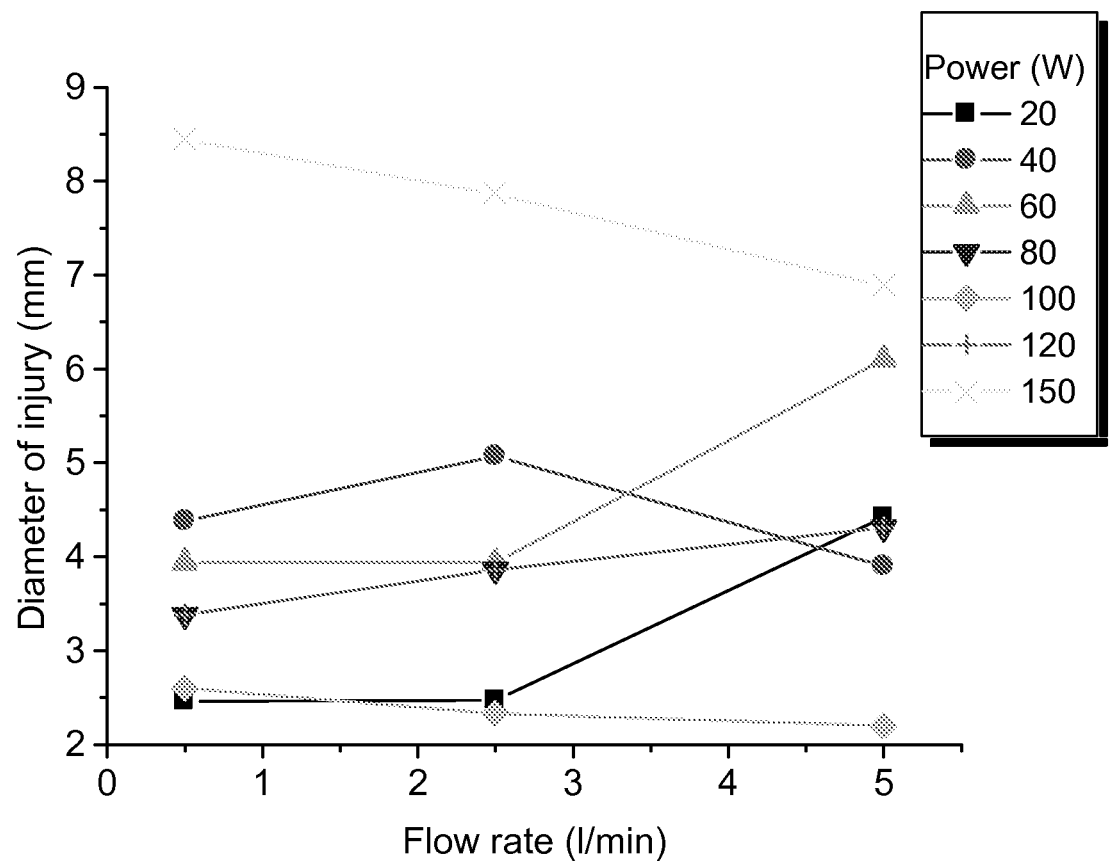
Figure 17B:
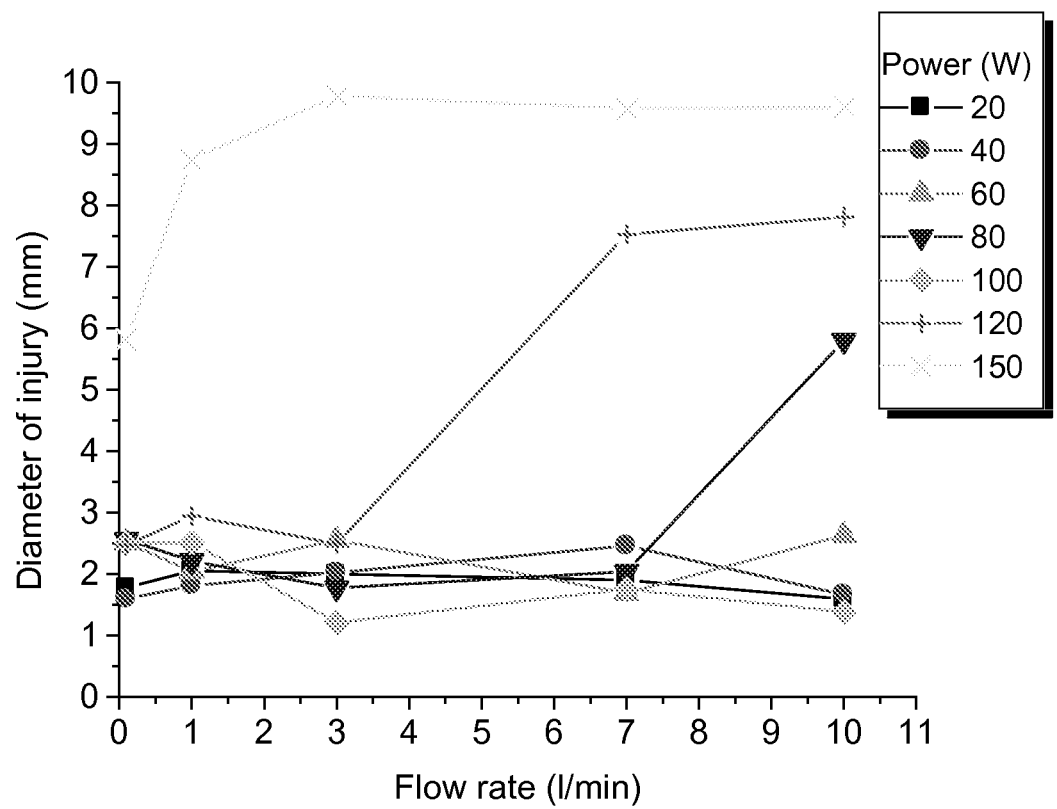

The pig's liver samples were treated by the hybrid plasma scalpel as following. In coagulation mode, the pig's liver sample was treated by 5 consecutive applications of the hybrid plasma scalpel to the same point of the liver sample (total treatment duration was ~5 s). The thermocouple was located about 3 mm under the treated point as shown in FIG. 3A. In cut mode, a 5 mm straight cut in the pig's liver sample was created by five consecutive passes with hybrid plasma scalpel along the cut (total duration ~5 s) and thermocouple probe was located about 3 mm aside from the cut (see FIG. 3B). The hybrid plasma scalpel was used with both the Argon 2/SS-200E and Argon 4/SS601MCa systems with flow rates from 0.5 to 5 liters/minute and from 0.1, 3.0, 7.0 and 10.0 liter/minute respectively. Data and graphs of results from these experiments are shown in FIGS. 4-11 and 13-20 and images of the treated tissue are shown in FIGS. 12A-D and 21A-J.

Data and graphs for testing of each of the four operating modes are shown in the drawings as follows: i) conventional cut shown in FIGS. 6A-6B, 10A-B, 13A-B and 18A; (ii) conventional coagulation shown in FIGS. 4A-C, 14A-B and 18B; (iii) conventional argon plasma coagulation shown in FIGS. 5A-F, 9A-F, 15A-B and 18C; and (iv) hybrid plasma cut shown in FIGS. 7A-C, 11A-C, 16A-B, 17A-B (with Argon 4/SS601MCa), 18D and 18E (with Argon 4/SS601MCa). Graphs comparing performance in the various modes of operation are shown in the graphs in FIGS. 19A-D and 20A-C.

Figure 19A:
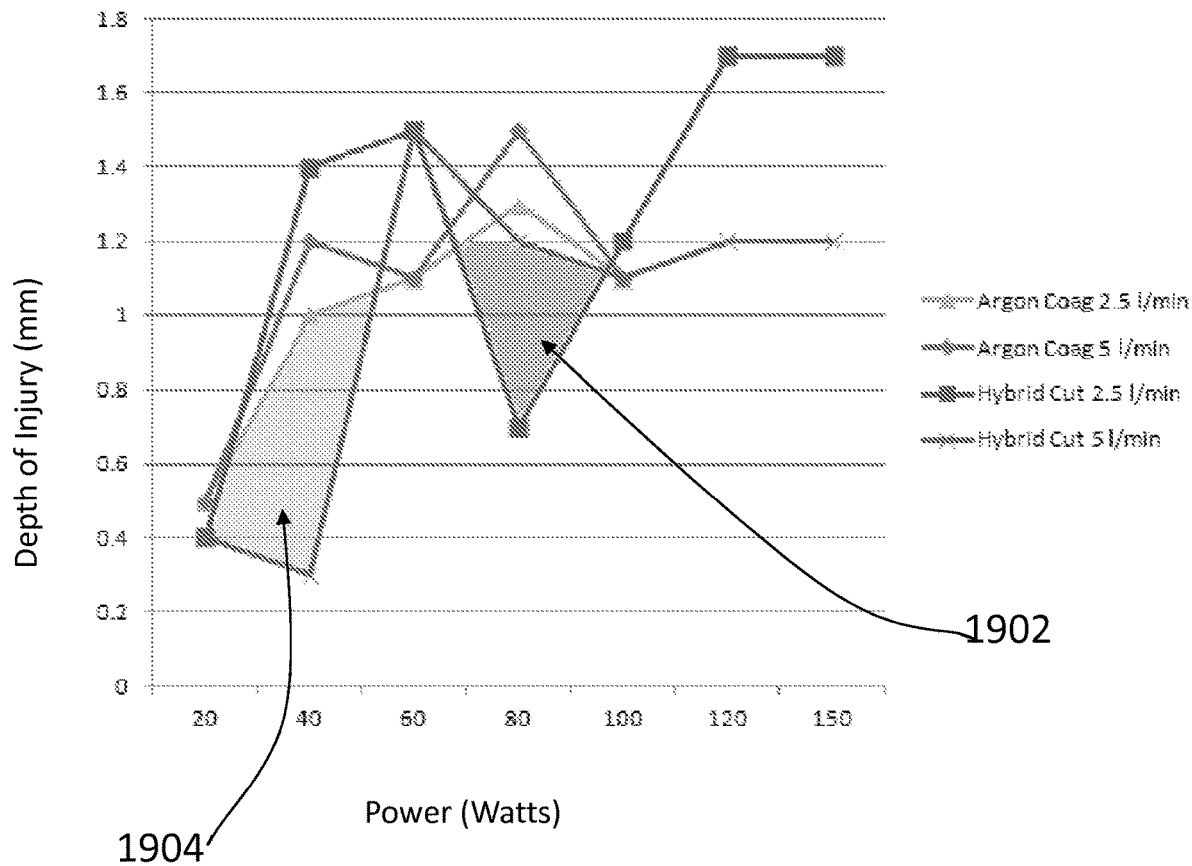
FIG. 19A is a graph comparing depth of injury data for a USMI SS-200E/Argon 2 system in argon plasma coagulation mode and in hybrid plasma cut mode.
Figure 19B:
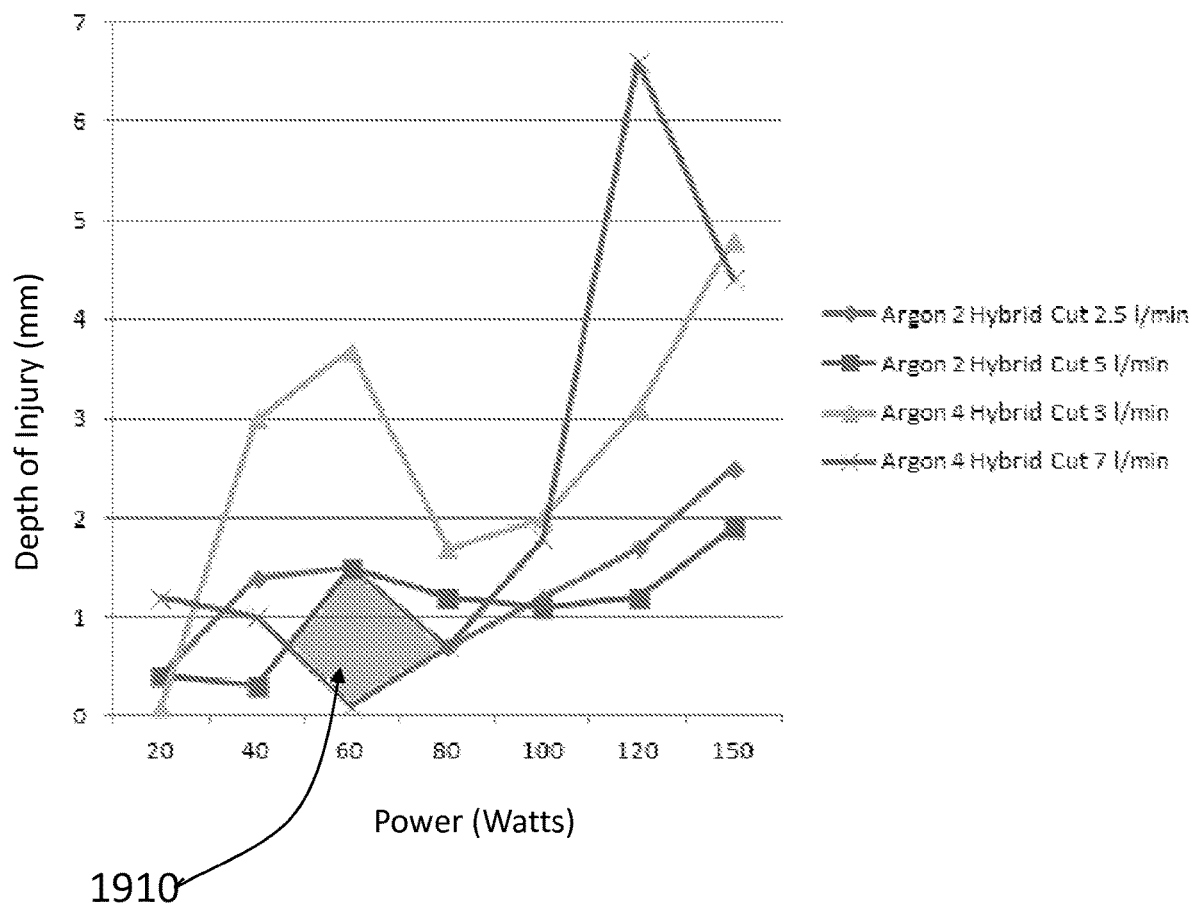
FIG. 19B is a graph comparing depth of injury data for a USMI SS-200E/Argon 2 system in hybrid plasma cut mode and a USMI SS-601MCa/Argon 4 system in hybrid plasma cut mode.
Figure 19C:
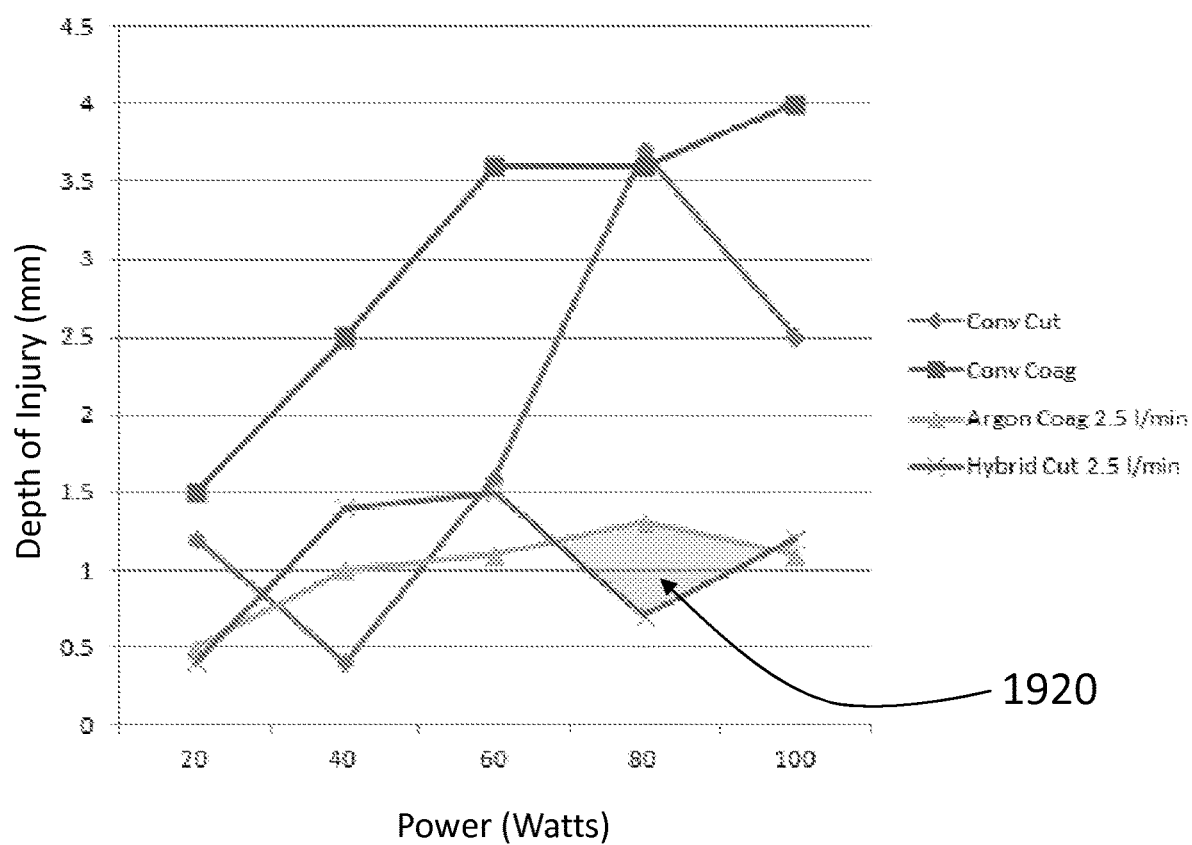
FIG. 19C is a graph comparing depth of injury data for a USMI SS-200E/Argon 2 system in conventional cut mode, conventional coagulation mode, argon plasma coagulation mode with a gas flow rate of 2.5 l/min and in hybrid plasma cut mode with a gas flow rate of 2.5 l/min.
Figure 19D:
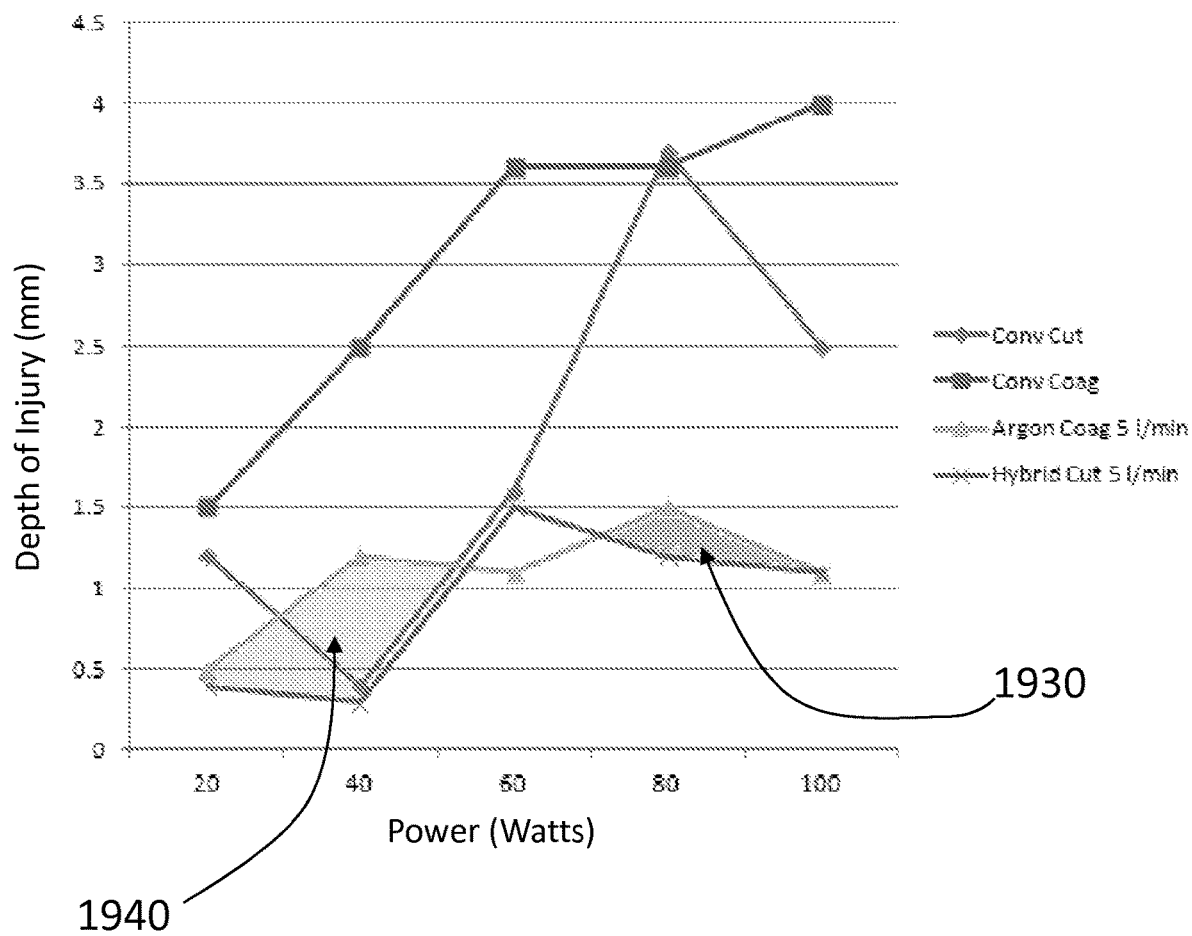
FIG. 19D is a graph comparing depth of injury data for a USMI SS-200E/Argon 2 system in conventional cut mode, conventional coagulation mode, argon plasma coagulation mode with a gas flow rate of 5 l/min and in hybrid plasma cut mode with a gas flow rate of 5 l/min.

FIGS. 19C-D show comparisons of the depth of injury found in the four modes of operation performed with the Argon 2/SS-200E system. FIG. 19C shows the comparison with both the conventional argon plasma coagulation mode and the hybrid plasma cut mode of the present invention at an argon flow rate of 2.5 L/min. FIG. 19D shows the comparison using an argon flow rate of 5 L/min. One can see form FIG. 19C that at lower power settings, e.g., below 70 W, and a flow rate of 2.5 L/min., the hybrid plasma cut mode of the present invention results in the depth of tissue injury being greater than the depth of injury in conventional argon plasma coagulation mode. Since the electrosurgical generator is in a cutting mode similar to (or identical to) conventional electrosurgical cutting when the hybrid plasma cut mode of the present invention is used, it is logical that it would result in a greater depth of injury than a conventional argon plasma coagulation mode. At mid to high power ranges, e.g. 70-100 W (see item 1920), however, the hybrid plasma cut mode of the present invention results in a smaller depth of injury than conventional argon plasma coagulation and conventional electrosurgical cutting. The result is vastly superior to conventional electrosurgical cutting (0.7-1.5 mm depth for hybrid plasma cut versus 2.5-3.7 mm for conventional cut) and significantly better than conventional APC (0.6 mm for plasma cut versus 1.2 mm for conventional APC). FIG. 19D shows similar results for an argon flow rate of 5 L/min. In lower power ranges (see item 1940) the depth of injury for hybrid plasma cut tends to track the depth of injury with conventional electrosurgical cutting. In mid to high power ranges, e.g., 70-100 W (see item 1930), however, the hybrid plasma cut mode of the present invention provides superior, i.e., smaller, depth of injury versus both conventional argon plasma coagulation (see item 1930) and conventional electrosurgical cutting.

FIG. 19A shows a comparison of the depth of injury in the hybrid argon cut mode of the present invention versus the conventional argon plasma coagulation mode at argon flow rates of 2.5 and 5.0 L/min. The graph in FIG. 19A shown that with the Argon 2/SS-200E system, the hybrid plasma cut mode of the present invention achieves a substantially superior result compared to conventional argon plasma coagulation at settings of about 70-90 W and 2.5 L/min (see item 1902) and 30-50 W at 5 L/min (see 1904). FIG. 19B shows a comparison of the hybrid plasma cut mode of the present invention performed with the two different test systems. In FIG. 19B, one can see that with the Argon 4/SS601MCa system, the hybrid plasma cut mode of the present invention achieves an unexpectedly superior result at settings of about 50-80 W and 7 L/min (see item 1910) but also is superior to conventional APC in the power range of 50-100 W at 7 L/min.

Figure 20A:
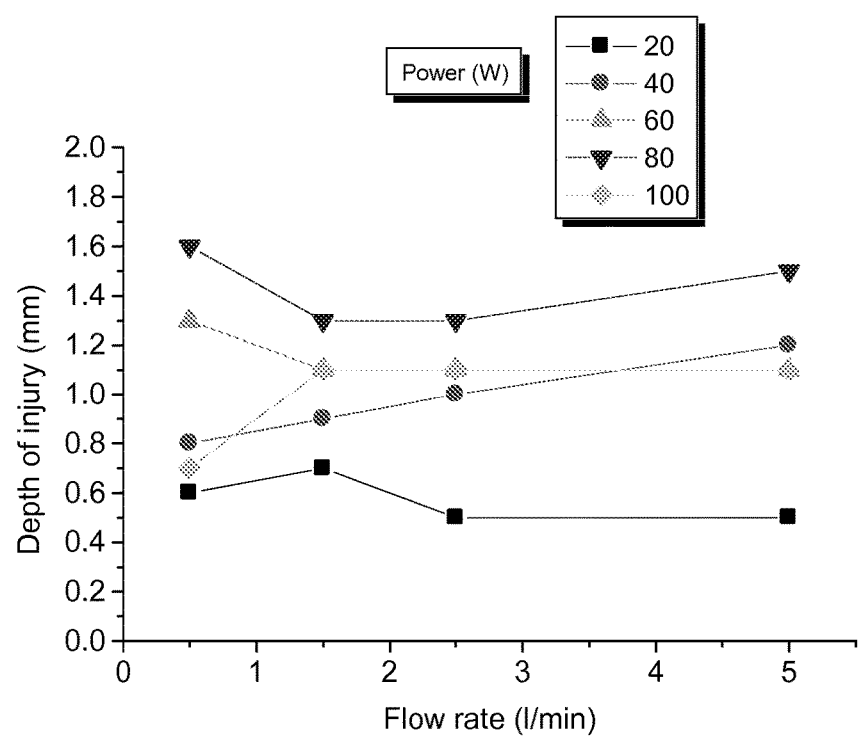
FIG. 20A is a graph of depth of injury data for a USMI SS-200E/Argon 2 in argon plasma coagulation mode.
Figure 20B:
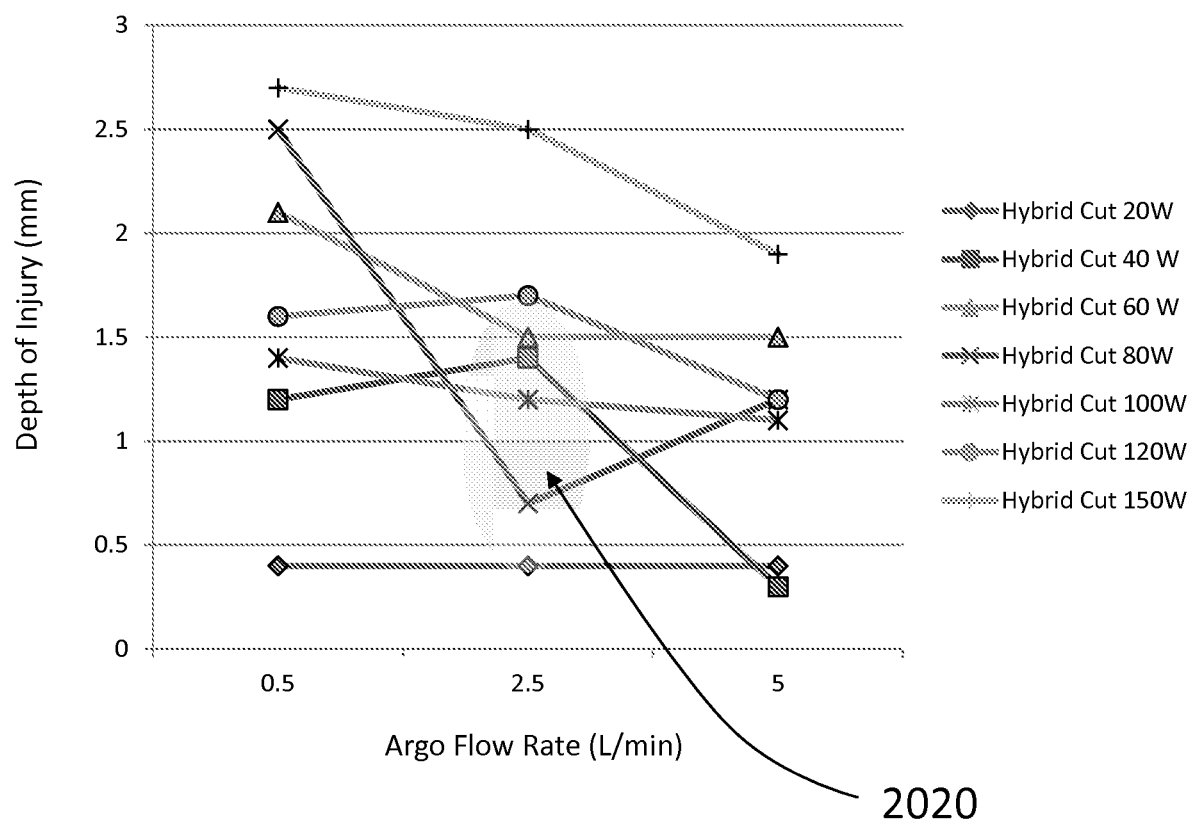
FIG. 20B is a graph of depth of injury data for a USMI SS-200E/Argon 2 in hybrid argon cut mode in accordance with a preferred embodiment of the present invention.
Figure 20C:
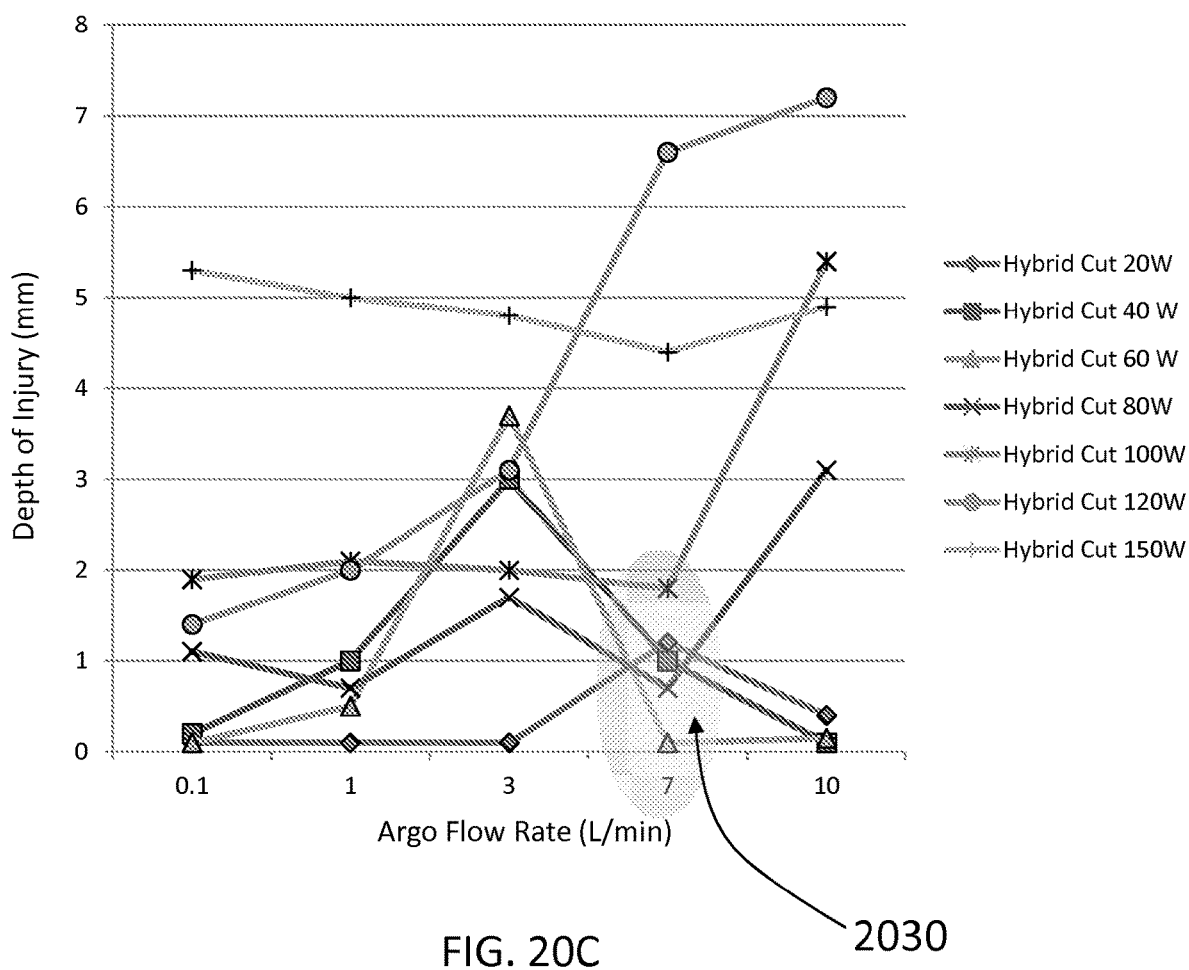
FIG. 20C is a graph of depth of injury data for a USMI SS-601MCa/Argon 4 system in hybrid argon cut mode in accordance with a preferred embodiment of the present invention.
Figure 21A:
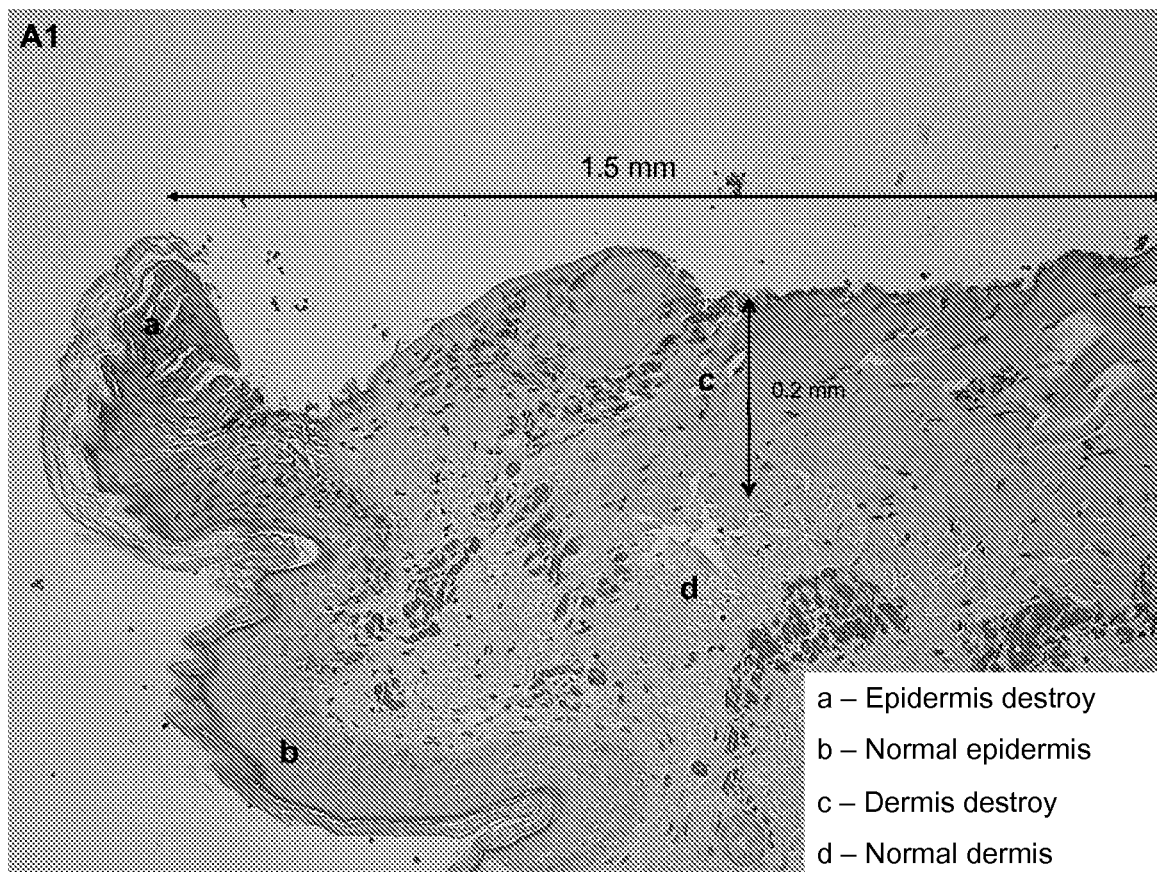
FIG. 21A is a tissue image of in vivo porcine skin Hybrid Plasma cut 20 w@3 liters/min, 2 sec., depth of injury 0.2 mm, eschar 1.5 mm.
Figure 21B:
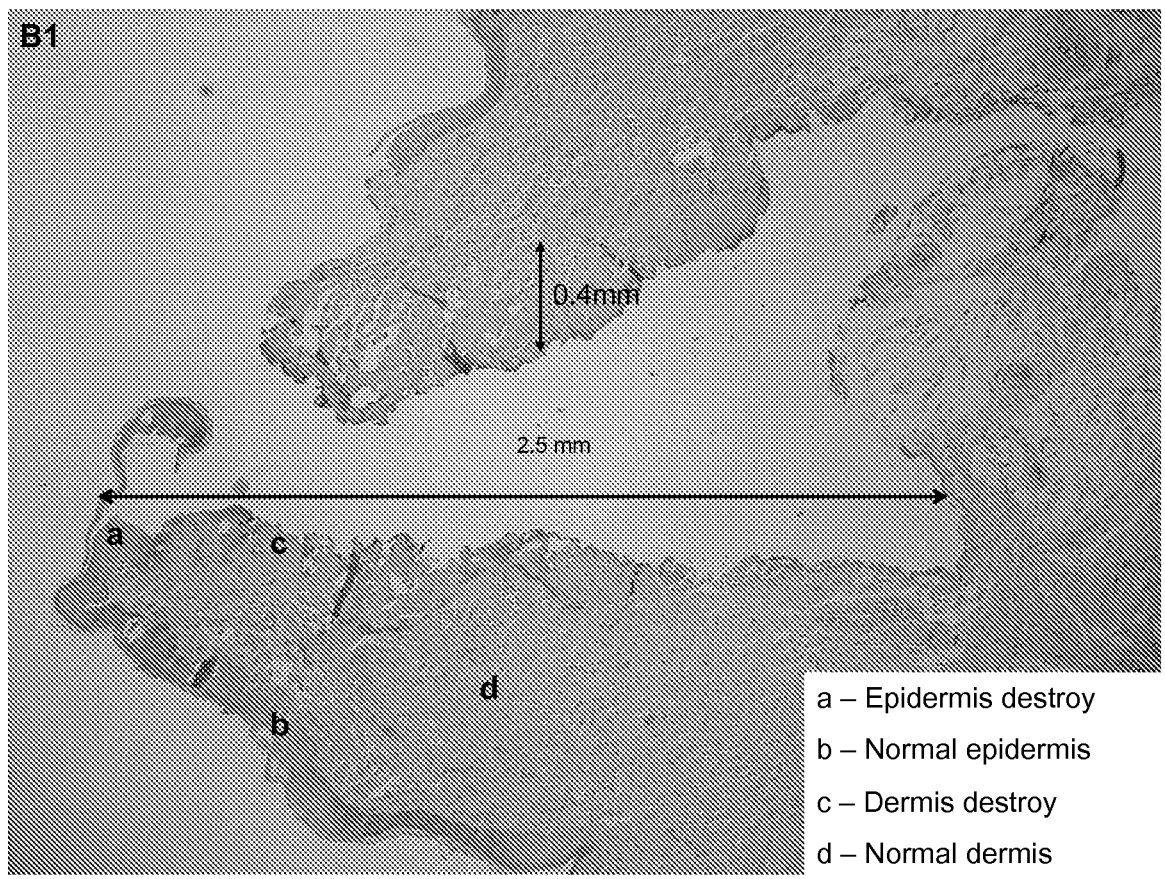
FIG. 21B is a tissue image of in vivo skin Conventional Cut: 20 w@3 liters/min, 2 sec. depth of injury (0.4 mm), eschar (2.5 mm).
Figure 21C:
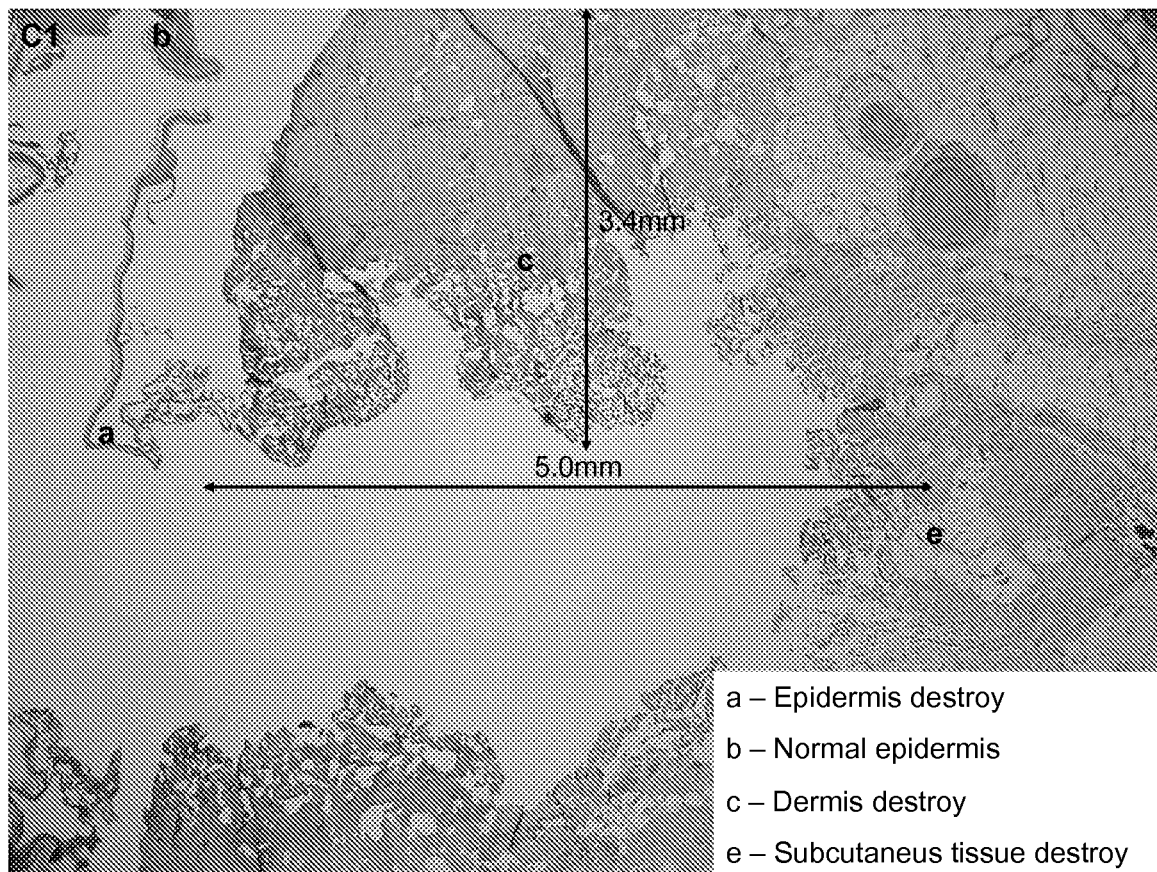
FIG. 21C is a tissue image of in vivo Conventional Coagulation: 20 w@3 liters/min, 2 sec., depth of injury (3.4 mm), eschar (5.0 mm).
Figure 21D:
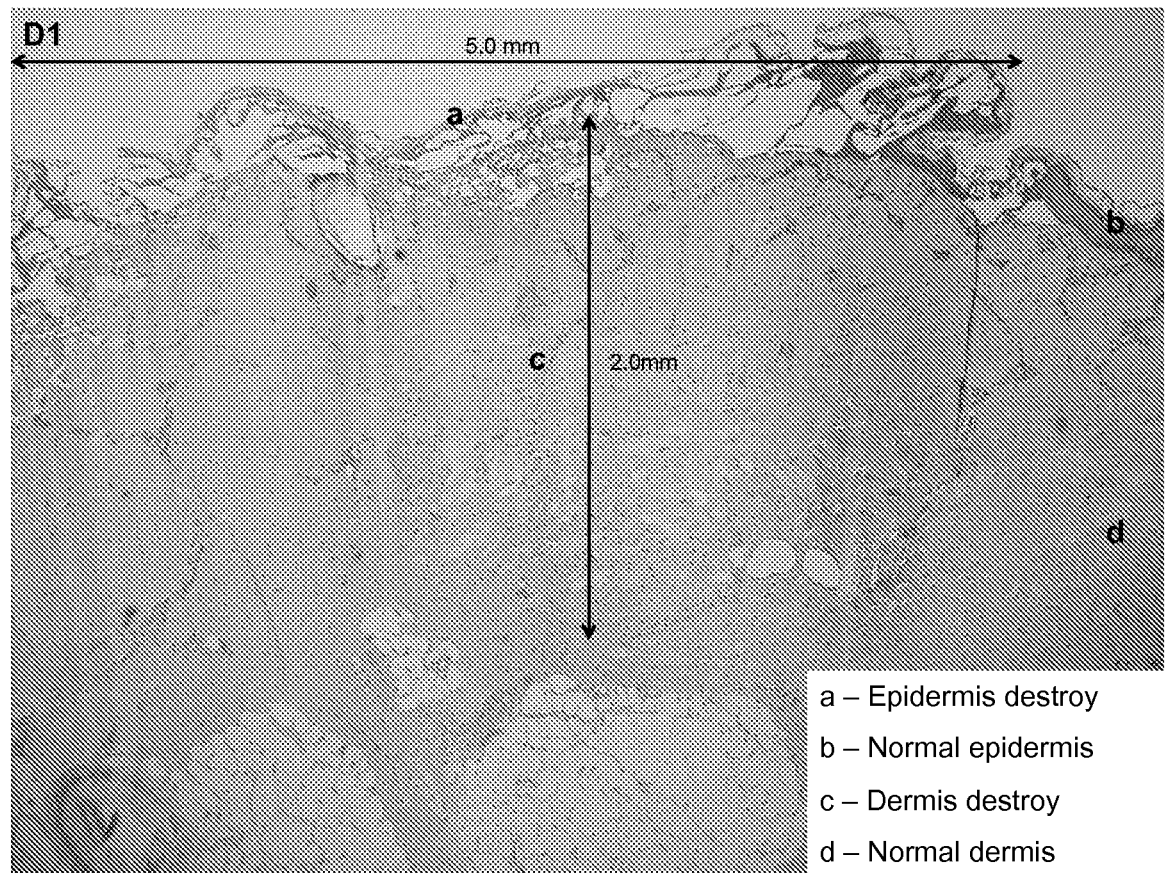
FIG. 21D is a tissue image of Argon Plasma Coagulation: 20 w@3 liters/min, 2 sec., depth of injury 2.0 mm, eschar 5.0 mm.
Figure 21E:
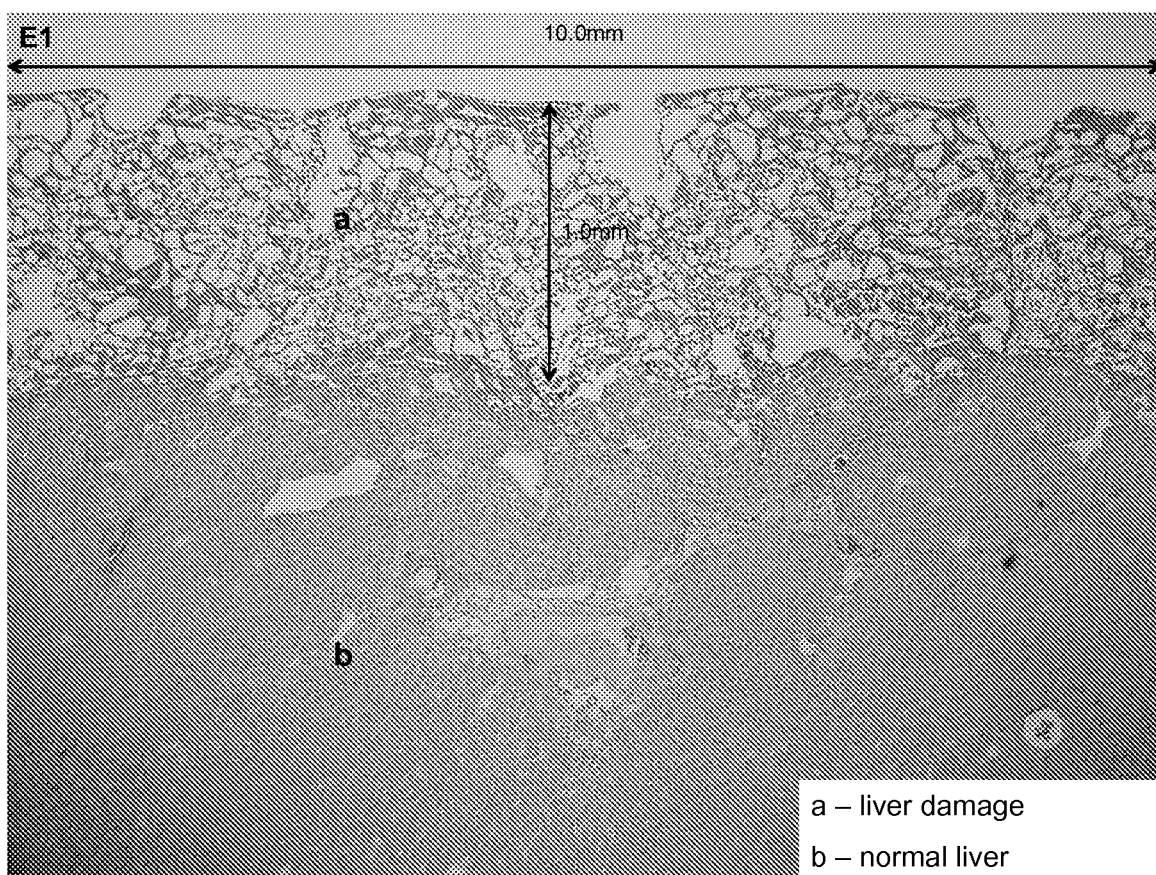
FIG. 21E is a tissue image of Argon Plasma Coagulation: depth of injury (1.0 mm), eschar (10.0 mm) @40 w, 3 liters/min.
Figure 21F:
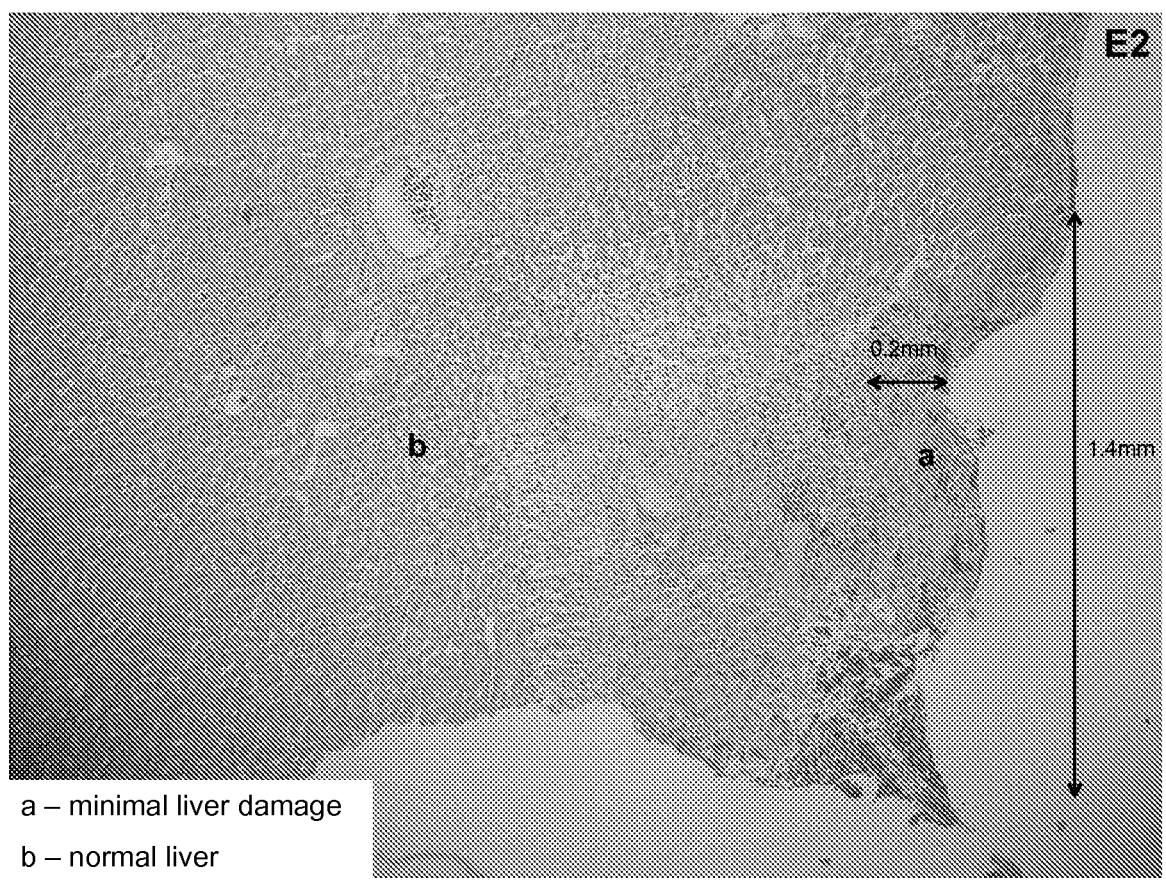
FIG. 21F is a tissue image of in vivo Hybrid Plasma cut: depth of injury (0.2 mm), Eschar (1.4 mm), 40 w@3 Liters/min.
Figure 21G:
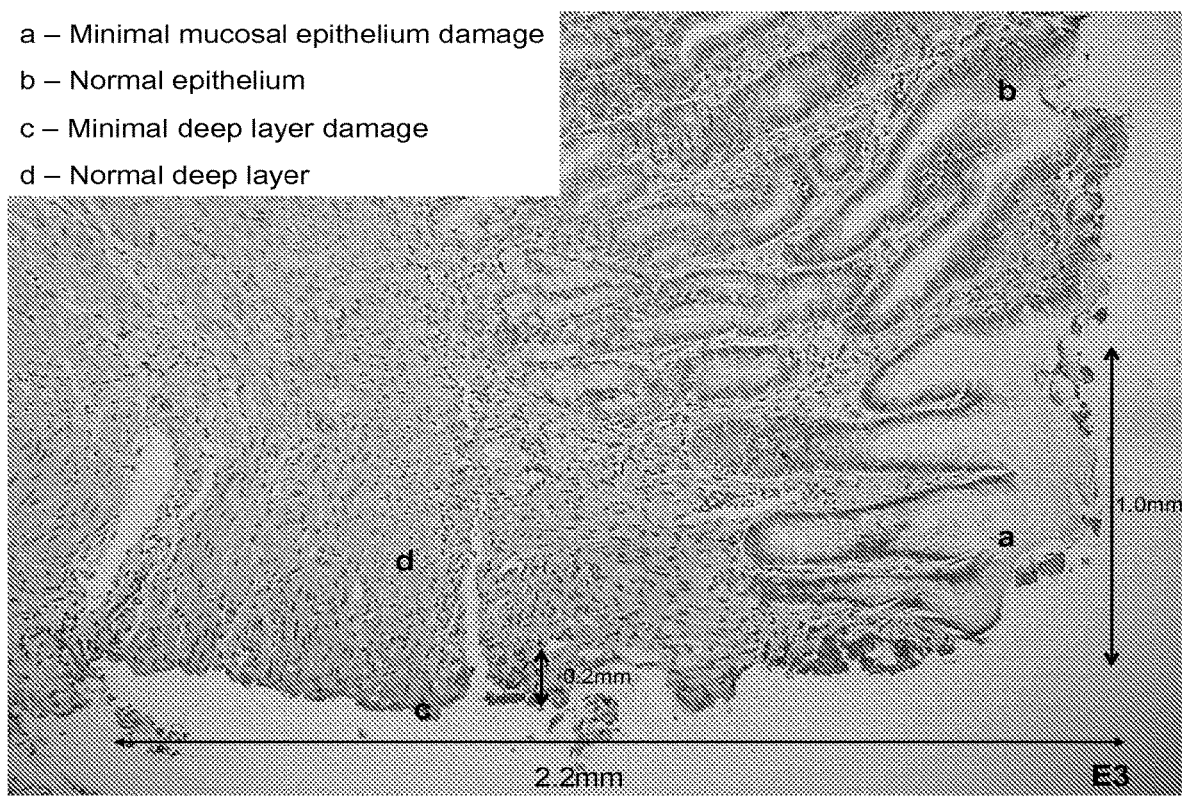
FIG. 21G is a tissue image of in vivo porcine resection of $1^{st}$ part of Duodenum with Hybrid plasma cut, depth of Injury (0.2 mm) eschar (1.0 mm) @40 w, 3 liters/min, 3 sec.
Figure 21H:
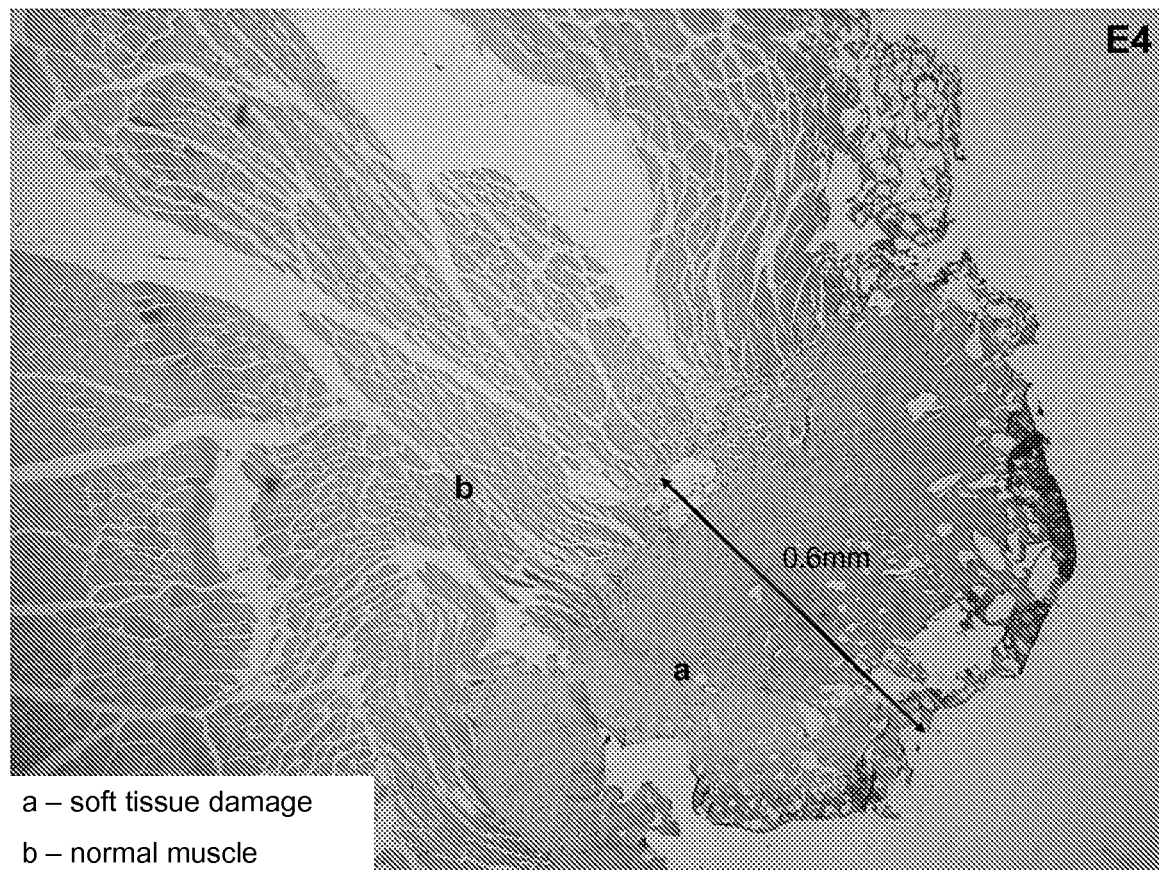
FIG. 21H is a tissue image of in vivo porcine resection of Sternum: depth of injury 0.6 mm, 120 w@5 liters/min.
Figure 21I:
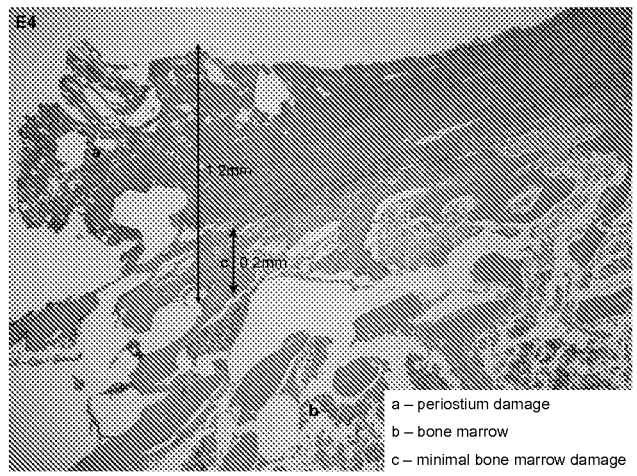
FIGS. 21I and 21J is a tissue image of in vivo resection of sternum in vivo porcine model minimal bone marrow damage (0.2 mm) @120 w, 5 liters/min.
Figure 21J:
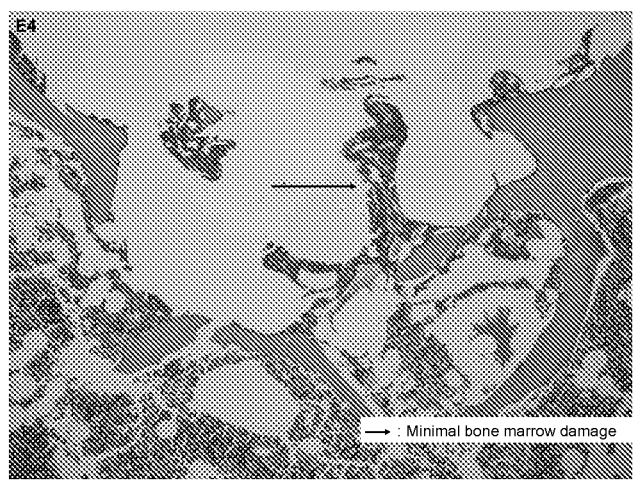

As shown in FIG. 20A, the depth of injury associated with conventional argon plasma coagulation is not very dependent upon the argon flow rate. As each power level tested on the Argon 2/SS-200E system in conventional APC mode, the depth of injury varied only by a small amount (approximately <2 mm) at each flow rate tested. In contrast, in the hybrid plasma cut mode of the present invention, significant variations in the depth of injury were found at various combinations of power and argon flow rate as shown in FIGS. 20B and 20C. In FIG. 20B, it can be seen that at higher power levels of 60-100 W on the Argon 2/SS-200E system in hybrid plasma cut mode, the depth of injury decreases dramatically in the argon flow rate range 2020 of 1-3 L/min at a power level of 100 W decreases steadily as the flow rate increases up the 5 L/min., which was the highest flow rate tested on that system. With that system, the graph in FIG. 20B shows a particular beneficial effect at a power level of about 80 W and an argon flow rate of about 2.5 L/min. In FIG. 20C, it similarly can be seen that at higher power levels of 60-100 W on the Argon 4/SS601MCa system in hybrid plasma cut mode the depth of injury decreases dramatically in the argon flow rate range 2030 of 6-8 L/min. In can be seen in the graph of FIG. 20C that with this more powerful system, a particularly beneficial effect is achieved with power levels of 60-100 W and an argon flow rate of approximately 7.0 L/min.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An electrosurgical device comprising:
a housing;
electrode tubing in said housing;
a port at a proximal end of said electrode tubing for connecting a channel in said electrode tubing to a source of pressurized inert gas;
a port at a distal end of said housing for discharging inert gas flowing through said channel;
an electrode extending through said housing;
a fiberglass plate in said housing;
an electrical connector connected to said electrode and said fiberglass plate, wherein said electrical connector is configured to connect to an electrosurgical generator;
controls in said housing for controlling application of electrical energy to said electrode and controlling a flow of gas into said channel from said source of pressurized inert gas, said controls comprising two buttons extending through a side of said housing; and
a sliding control member extending out of a slot in a side of said housing wherein said sliding control member is movable between a first position in which a distal end of said electrode is within a distal end of said housing and a second position in which said distal end of said electrode extends out of said distal end of said housing.

2. An electrosurgical device comprising:
a housing;
electrode tubing in said housing, said electrode tubing comprising an electrode and a channel having a proximal end and a distal end;
a gas connector configured to connect said channel in said electrode tubing to a source of pressurized gas;
an electrical connector configured to connect a proximal end of said electrode to an electrosurgical generator;
an electrosurgical blade connected to a distal end of said electrode;
a ceramic tip at a distal end of said housing, said ceramic tip having a proximal end through which flowing gas from said channel in said electrode tubing enters said ceramic tip and a distal end out of which said flowing gas exits said ceramic tip;
controls in said housing for controlling application of electrical energy to said electrode and controlling a flow of gas into said channel from said source of pressurized inert gas, said controls comprising at least two buttons extending through a side of said housing; and
a slidable control member extending through an elongated opening in a side of said housing, wherein said slidable control member moves said housing and said surgical blade relative to one another to place said surgical blade a first position in which said electrosurgical blade extends out of said distal end of said ceramic tip and a second position in which said electrosurgical blade does not extend out of said distal end of said ceramic tip.

3. The electrosurgical device of claim 2 further comprising tubing extending from a proximal end of said housing to said gas connector.

4. The electrosurgical device of claim 2 wherein said slidable control member extends through and is movable along a slot in said housing.

* * * * *